United States Patent
Williams, Sr.

(10) Patent No.: US 12,358,892 B2
(45) Date of Patent: Jul. 15, 2025

(54) METALLOENZYME INHIBITORS FOR TREATING CANCERS, ALZHEIMER'S DISEASE, HEMOCHROMATOSIS, AND OTHER DISORDERS

(71) Applicant: Miralogx LLC, Tampa, FL (US)

(72) Inventor: Jonnie R. Williams, Sr., Sarasota, FL (US)

(73) Assignee: Miralogx LLC, Tampa, FL (US)

( * ) Notice: Subject to any disclaimer, the term of this patent is extended or adjusted under 35 U.S.C. 154(b) by 199 days.

(21) Appl. No.: 18/134,843

(22) Filed: Apr. 14, 2023

(65) Prior Publication Data

US 2023/0295125 A1    Sep. 21, 2023

Related U.S. Application Data

(63) Continuation-in-part of application No. PCT/US2021/055327, filed on Oct. 16, 2021.

(60) Provisional application No. 63/092,594, filed on Oct. 16, 2020.

(51) Int. Cl.
   *C07D 401/14*   (2006.01)
   *A61P 29/00*    (2006.01)
   *A61P 35/00*    (2006.01)
   *C07D 401/04*   (2006.01)

(52) U.S. Cl.
   CPC ............ *C07D 401/14* (2013.01); *A61P 29/00* (2018.01); *A61P 35/00* (2018.01); *C07D 401/04* (2013.01)

(58) Field of Classification Search
   CPC ..... C07D 401/04; C07D 401/14; A61P 29/00; A61P 35/00
   See application file for complete search history.

(56) References Cited

U.S. PATENT DOCUMENTS

2018/0258095 A1    9/2018    Hert et al.

FOREIGN PATENT DOCUMENTS

WO    2020/146532 A1    7/2020

OTHER PUBLICATIONS 3,5-Bis(3,4-dihydro-2H-pyrrol-5-yl)pyridine (Year: 2017).*
National Center for Biotechnology Information (2023). PubChem Substance Record for SID 11514478, CDS1_002904, Source: ChemBank, available on Jun. 5, 2006. <https://pubchem.ncbi.nlm.nih.gov/substance/11514478>.
National Center for Biotechnology Information (2023). PubChem Substance Record for SID 11673691, SID 11673691, Source: DiscoveryGate, available on Jul. 16, 2006. <https://pubchem.ncbi.nlm.nih.gov/substance/11673691>.
National Center for Biotechnology Information (2023). PubChem Substance Record for SID 132915369, AKOS006632742, Source: AKos Consulting & Solutions, available on Jan. 25, 2012. <https://pubchem.ncbi.nlm.nih.gov/substance/132915369>.
Sep. 26, 2024—(EP) Search Report—App 21881249.3.
PubChem Identifier: CID 125294604; 3,5-Bis(3,4-dihydro-2H-pyrrol-5-yl)pyridine, originally submitted Apr. 10, 2017.

* cited by examiner

*Primary Examiner* — Erich A Leeser
(74) *Attorney, Agent, or Firm* — Banner & Witcoff, Ltd.

(57) ABSTRACT

Pharmaceutical compounds have anti-inflammatory activity and, in some aspects, may function as metalloenzyme inhibitors for the beneficial regulation of metalloproteins. A pharmaceutical composition may include a therapeutically effective amount of the compound(s) and a pharmaceutically acceptable vehicle. The pharmaceutical compositions may be useful for treating a disorder associated with chronic inflammation and/or metalloenzyme misregulation, including hemochromatosis, cancers such as breast cancer, or neurodegenerative diseases such as Alzheimer's disease.

2 Claims, 12 Drawing Sheets

METALLOENZYME INHIBITORS FOR TREATING CANCERS, ALZHEIMER'S DISEASE, HEMOCHROMATOSIS, AND OTHER DISORDERS

CROSS REFERENCE TO RELATED APPLICATION

This application is a continuation-in-part of International Patent Application No. PCT/US2021/055327, filed Oct. 16, 2021, which claims priority under 35 U.S.C. § 119(e) to U.S. Application No. 63/092,594, filed Oct. 16, 2020. The contents of these applications are hereby incorporated by reference in their entirety.

BACKGROUND

Metalloproteins perform a number of functions in vivo, examples of which include regulating blood pH, facilitating matrix degradation, and modulating DNA transcription. Metalloenzyme misregulation contributes to a variety of disease states, examples of which include cancers, heart disease, Alzheimer's disease, and hemochromatosis. Metalloenzyme inhibition thus presents a promising target for a variety of therapeutic treatments.

Conventional metalloenzyme inhibitors typically are small molecules that incorporate a metal binding group (MBG) to coordinate the active site metal ion. The MBG is appended to a druglike "backbone" group via a linker. Hydroxamic acid is the most common MBG for metalloenzyme inhibitors, followed by carboxylic acids, thiols, and phosphonates.

There remains a need for alternative metalloenzyme inhibitors and therapeutic treatments for cancers, such as breast cancer, and other disorders associated with metalloenzyme misregulation, such as hemochromatosis and Alzheimer's disease.

SUMMARY

According to one aspect, a compound has the structure:

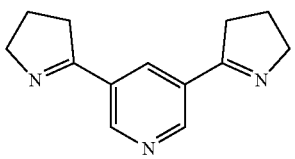

or a pharmaceutically acceptable salt, ester, or solvate thereof.

In some embodiments, the compound has the structure:

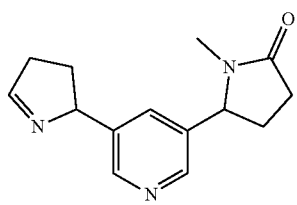 [SMILES: CN1C(=O)CCC1c1cncc(C2CCC=N2)c1]

or a pharmaceutically acceptable salt, ester, or solvate thereof.

In some embodiments, the compound has the structure:

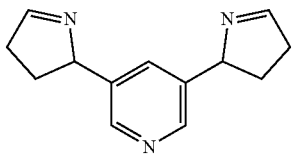 [SMILES: C1=NC(c2cncc(C3CCC=N3)c2)CC1]

or a pharmaceutically acceptable salt, ester, or solvate thereof.

In some embodiments, the compound has the structure:

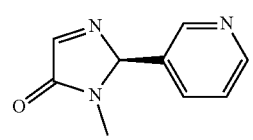

or a pharmaceutically acceptable salt, ester, or solvate thereof.

In some embodiments, the compound has the structure:

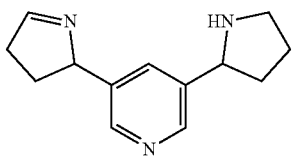 [SMILES: C1=NC(c2cncc(C3CCCN3)c2)CC1]

or a pharmaceutically acceptable salt, ester, or solvate thereof.

In some embodiments, the compound has the structure:

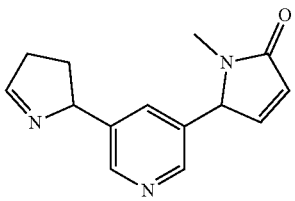 [SMILES: CN1C(=O)C=CC1c1cncc(C2CCC=N2)c1]

or a pharmaceutically acceptable salt, ester, or solvate thereof.

In another aspect, a pharmaceutical composition comprises a therapeutically effective amount of the above-depicted compound and a pharmaceutically acceptable vehicle therefor.

In another aspect, a method of treating a disorder associated with chronic inflammation comprises administering the pharmaceutical composition to an individual in need thereof. In yet another aspect, a method of treating a disorder associated with metalloenzyme misregulation comprises administering the pharmaceutical composition to an individual in need thereof. In some aspects, the disorder is a cancer such as breast cancer. In some embodiments, the cancer is breast cancer, colorectal cancer, or non-small cell lung cancer (NSCLC).

In other aspects, the disorder is hemochromatosis. In yet other aspects, the disorder is a neurodegenerative disorder such as Alzheimer's disease.

Various other pharmaceutical compounds, pharmaceutical compositions, and associated treatment methods are also described herein.

BRIEF DESCRIPTION OF THE DRAWINGS

Non-limiting and non-exhaustive embodiments are described with reference to the following figures, wherein like reference numerals refer to like parts throughout the various views unless otherwise specified.

DETAILED DESCRIPTION

Figure 1:
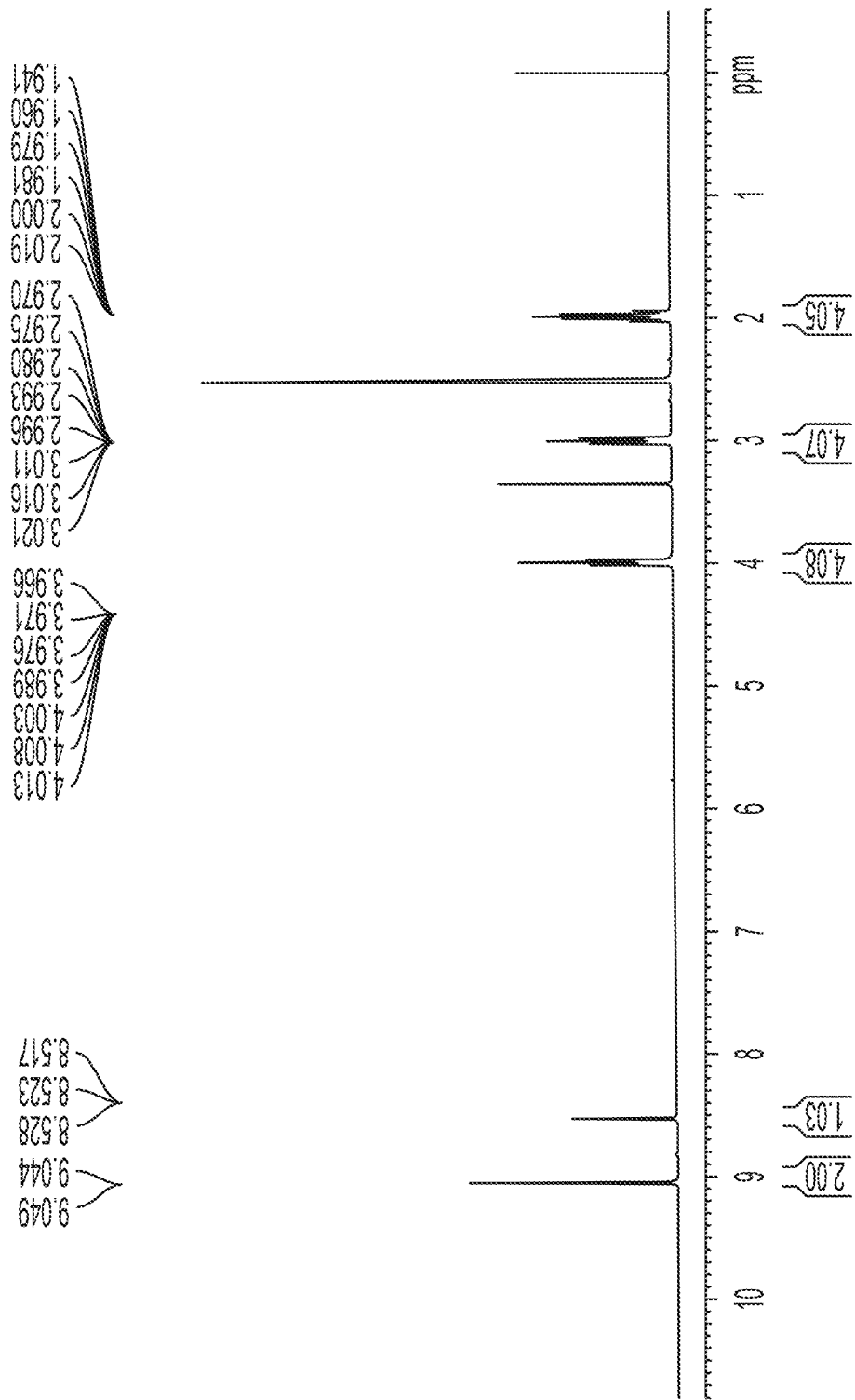
FIG. 1 is a nuclear magnetic resonance (NMR) spectrum for a synthetically prepared compound in accordance with one aspect of the present disclosure.

In some aspects, the pharmaceutical compounds disclosed herein may function as metalloenzyme inhibitors. While not wanting to be bound by theory, it is believed that the compounds may beneficially regulate metalloproteins and/or inhibit metalloenzymes to treat disorders associated with the overexpression, enhanced activation, or misregulation of an endogenous metalloenzyme. Broadly, the compounds may interact with one or more of the metalloenzyme targets as described in Chen et al., Targeting Metalloenzymes for Therapeutic Intervention, Chem Rev. 2019 Jan. 23; 119(2): 1323-1455, doi:10.1021/acs.chemrev.8b00201, the disclosure of which is hereby incorporated by reference. Zinc enzymes, as a part of zinc metalloproteins, occupy a pivotal position in this field.

Zinc is an essential transition metal ion and a micronutrient in life, and is necessary for the activity of more than 300 enzymes. The concentration of zinc in cells is quite high, almost as high as that of ATP. In biology, it is the second most common metal, and the only one known to be present in all six classes of enzymes. Zinc is the primary metal cofactor of metalloproteins, and zinc-containing proteins (up to 3,000) are the largest category of metalloproteins, which are in the range of one quarter to a half of all metalloproteins. Zinc metalloproteins are implicated in many important biological functions, including cell proliferation and differentiation, RNA and DNA synthesis, cell structure/membrane stabilization, and redox regulation and apoptosis. Accumulating evidence has indicated that zinc metalloproteins play fundamental roles in the patho-physiology and pathogenesis of a wide range of human diseases, from cancer to infections. See Hou et al., "Zinc enzymes in medicinal chemistry," *Euro. J. of Med. Chem.* 226 (2021) 113877.

Zinc also is one of the most prevalent and essential elements involved in brain function, and it plays a role in both physiological and pathophysiological processes. Neurons containing "free ionic zinc" ($Zn^{2+}$) are found in various areas of the brain, including the cortex, amygdala, olfactory bulb, and hippocampal neurons, which appear to have the highest concentration of zinc in the brain. Zinc has been implicated in the biological activity of enzymes, proteins, and signal transcription factors, as well as in the maintenance of various homeostatic mechanisms, acting as structural, regulatory, and catalytic cofactors for a variety of enzymes, such as DNA and RNA polymerases, histone deacetylases, and DNA ligases. Zinc is also important for cell growth and genomic stability. See Choi et al., "Zinc in the Brain: Friend or Foe?," *Int. J. Mol. Sci.* 2020, 21, 8941; doi:10.3390/ijms21238941.

The pharmaceutical compounds disclosed herein have anti-inflammatory activity. For example, a compound may have an anti-inflammatory activity capable of reducing the levels of an inflammation-inducing molecule. While not wanting to be bound by theory, it is believed that the disclosed compounds may have an anti-inflammatory activity capable of reducing the levels of substance P(SP), calcitonin gene-related peptide (CGRP), glutamate, or a combination thereof. A compound may have an anti-inflammatory activity capable of reducing the levels of SP, CGRP, glutamate, or a combination thereof released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

Prostaglandins mediate a local inflammatory response and are involved in all inflammatory functions through action on prostaglandin receptors and mediate inflammatory signaling including chemotaxis (macrophages, neutrophils and eosinophils), vasodilation and algesia. However, the PG-mediated inflammatory response is self-limiting (resolving). The principle resolution factor is a prostaglandin called 15dPGJ2, which is an endogenous agonist of peroxisome proliferator-activator receptor-γ (PPAR-γ) signaling. PPAR-γ signaling pathway 1) induces apoptosis of macrophage M1 cells, thereby reducing the levels of Th1 pro-inflammatory cytokines and 2) promotes differentiation of monocytes into macrophage M2 cells. Macrophage M2 cells produce and release Th2 anti-inflammatory cytokines.

Compounds disclosed herein may have an anti-inflammatory activity capable of reducing the levels of an inflammation inducing prostaglandin. A compound may have an anti-inflammatory activity capable of reducing the levels of an inflammation inducing prostaglandin released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. A compound may have an anti-inflammatory activity capable of reducing the levels of an inflammation inducing prostaglandin released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The peroxisome proliferator-activated receptors (PPARs) are a group of nuclear receptor proteins that function as transcription factors regulating the expression of genes. All PPARs are known to heterodimerize with the retinoid X receptor (RXR) and bind to specific regions on the DNA of target genes called peroxisome proliferator hormone response elements (PPREs). PPARs play essential roles in the regulation of cellular differentiation, development, and metabolism (carbohydrate, lipid, protein), and tumorigenesis of higher organisms. The family comprises three members, PPAR-α, PPAR-γ, and PPAR-δ (also known as PPAR-β). PPAR-α is expressed in liver, kidney, heart, muscle, adipose tissue, as well as other tissues. PPAR-δ is expressed in many tissues but markedly in brain, adipose tissue, and skin. PPAR-γ comprises three alternatively-spliced forms, each with a different expression pattern. PPAR-γ1 is expressed in virtually all tissues, including heart, muscle, colon, kidney, pancreas, and spleen. PPAR-γ2 is expressed mainly in adipose tissue. PPAR-γ3 is expressed in macrophages, large intestine, and white adipose tissue. Endogenous ligands for the PPARs include free fatty acids and eicosanoids. PPAR-γ is activated by PGD2 (a prostaglandin), whereas PPAR-α is activated by leukotriene B4.

A compound may have an anti-inflammatory activity capable of reducing the levels of IFN-γ, TNF-α, IL-12, or a combination thereof released from a Th1 cell and increasing the levels of IL-10 released from a Th2 cell. A compound may have an anti-inflammatory activity capable of reducing the levels of IFN-γ, TNF-α, IL-12, or a combination thereof released from a Th1 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%, and capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A compound may have an anti-inflammatory activity capable of stimulating some or all PPAR signaling pathways. It is contemplated that such a compound therefore may act as a PPAR pan-agonist or possibly as a selective PPAR agonist.

A compound may have an anti-inflammatory activity capable of modulating Th1 and Th2 cytokines. A compound may have an anti-inflammatory activity capable of reducing the levels of Interferon-γ (IFN-γ), tumor necrosis factor-α (TNF-α), interleukin-12 (IL-12), or a combination thereof released from a Th1 cell. A compound may have an anti-inflammatory activity capable of reducing the levels of IFN-γ, TNF-α, IL-12, or a combination thereof released from a Th1 cell by, e.g., at least 10%, at least 20%, at least 30%, at least 40%, at least 50%, at least 60%, at least 70%, at least 80%, or at least 90%. A compound may have an anti-inflammatory activity capable of reducing the levels of IFN-γ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90.

A compound may have an anti-inflammatory activity capable of increasing the levels of IL-10 released from a Th2 cell. A compound may have an anti-inflammatory activity capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

According to one aspect, a compound has the structure:

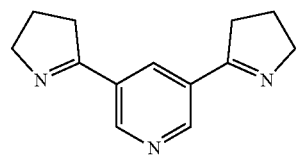 [SMILES: c1ncc(C2=NCCC2)cc1C1=NCCC1]

or a pharmaceutically acceptable salt, ester, or solvate thereof. In some embodiments, this compound is referred to as 3,5-bis(3,4-dihydro-2H-pyrrol-5-yl)pyridine.

In some embodiments, the compound comprises 3,5-bis(3,4-dihydro-2H-pyrrol-2-yl)pyridine. In some embodiments, the compound has the structure:

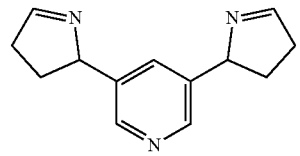

3,5-bis(3,4-dihydro-2H-pyrrol-2-yl)pyridine or a pharmaceutically acceptable salt, ester, or solvate thereof.

Another compound disclosed herein, 5-(5-(3,4-dihydro-2H-pyrrol-2-yl)pyridin-3-yl)-1-methylpyrrolidin-2-one, has the structure:

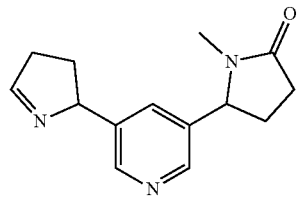 [SMILES: CN1C(=O)CCC1c1cncc(C2CCC=N2)c1]

or a pharmaceutically acceptable salt, ester, or solvate thereof.

In other aspects, a compound has a structure selected from the group consisting of:

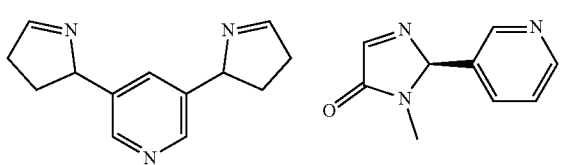

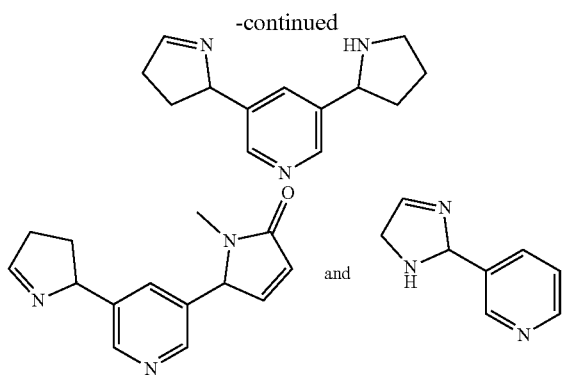

or a pharmaceutically acceptable salt, ester, or solvate thereof.

In some embodiments, the compound has the structure:

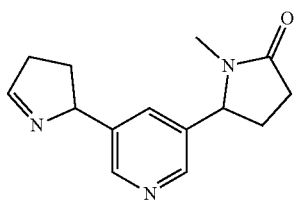 [SMILES: CN1C(=O)CCC1c1cncc(C2CCC=N2)c1]

or a pharmaceutically acceptable salt, ester, or solvate thereof.

In some embodiments, the compound has the structure:

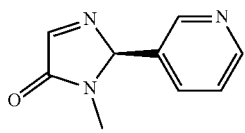

or a pharmaceutically acceptable salt, ester, or solvate thereof.

In some embodiments, the compound has the structure:

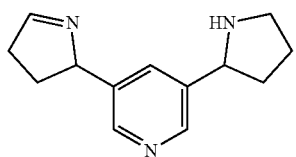 [SMILES: C1=NC(c2cncc(C3CCCN3)c2)CC1]

or a pharmaceutically acceptable salt, ester, or solvate thereof.

A pharmaceutical composition may include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle," "stabilizer," "diluent," "additive," "auxiliary" or "excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A chronic inflammation symptom can be associated with a large, otherwise unrelated group of disorders which underlay a variety of diseases and disorders. The immune system is often involved with chronic inflammatory disorders, demonstrated in both allergic reactions and some myopathies, with many immune system disorders resulting in abnormal inflammation. Non-immune diseases with etiological origins in chronic inflammatory processes include cancer, atherosclerosis, and ischaemic heart disease. In some embodiments, the cancer is a solid tumor cancer. In some embodiments, the cancer comprises a breast cancer, a colon cancer, or a lung cancer. In some embodiments, the cancer is a leukemia. In some embodiments, the cancer is breast cancer, colorectal cancer, or non-small cell lung cancer (NSCLC).

In some embodiments, the present disclosure relates to a method of treating a cancer in a subject in need thereof, comprising administering a therapeutically effective amount of a compound disclosed herein or a pharmaceutical composition disclosed herein to the subject in need. In some embodiments, the cancer is selected from the group consisting of an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

Non-limiting examples of disorders exhibiting chronic inflammation as a symptom include, without limitation, acne, acid reflux/heartburn, age related macular degeneration (AMD), allergy, allergic rhinitis, Alzheimer's disease, amyotrophic lateral sclerosis, anemia, appendicitis, arteritis, arthritis, asthma, atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, Crohn's disease, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sarcopenia, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, and vulvitis.

Compounds intended for administration to humans or other mammals generally should have very high purity. Purity refers to the ratio of a compound's mass to the total sample mass following any purification steps. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

Compound described herein that exist in more than one optical isomer form (enantiomer) may be provided either as racemic mixture or by isolating one of the enantiomers, the latter case in which purity as described above may refer to enantiomeric purity.

The compounds described herein may be prepared synthetically using techniques such as those described in Riah et al., "Synthesis of Cotinine and Cotinine N-oxide: Evaluation of their Interaction with Nicotine in the Insecticidal Activity," *J. Nat. Prod. Letters*, Vol. 11 (1997), https://doi.org/10.1080/10575639708043755, with appropriate modifications to reagents to obtain the disclosed structures as will be apparent to persons skilled in the art with the aid of no more than routine experimentation.

In some aspects, a compound may be converted into a pharmaceutically acceptable salts using techniques well known to persons skilled in the art. For example, salts such as sodium and potassium salts may be prepared by treating the compound with a suitable sodium or potassium base, such as sodium hydroxide or potassium hydroxide, respectively. Esters and ethers of the compound may be prepared as described, e.g., in Advanced Organic Chemistry, 1992, 4th Edition, J. March, John Wiley & Sons, or J. Med. Chemistry, 1992, 35, 145-151.

Compositions as described herein may be administered orally, nasally, topically, subcutaneously, intramuscularly, intravenously, or by other modes of administration known to persons skilled in the art.

A pharmaceutical composition may optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Examples of auxiliaries and/or excipients that may be mentioned are cremophor, poloxamer, benzalkonium chloride, sodium lauryl sulfate, dextrose, glycerin, magnesium stearate, polyethylene glycol, starch, dextrin, lactose, cellulose, carboxymethylcellulose sodium, talc, agar-agar, mineral oil, animal oil, vegetable oil, organic and mineral waxes, paraffin, gels, propylene glycol, benzyl alcohol, dimethylacetamide, ethanol, polyglycols, tween 80, solutol HS 15, and water. It is also possible to administer the active substances as such, without vehicles or diluents, in a suitable form, for example, in capsules.

A pharmaceutical composition may comprise a therapeutic compound in an amount sufficient to allow customary administration to an individual. A unit dose form may have, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects, a unit dose form may have, e.g., at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may include, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg of a therapeutic compound. In still other aspects of this embodiment, a pharmaceutical composition disclosed herein may include, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg of a therapeutic compound.

Pharmaceutical compositions as described herein may include a pharmaceutically acceptable solvent. A solvent is a liquid, solid, or gas that dissolves another solid, liquid, or gaseous (the solute), resulting in a solution. Solvents useful in the pharmaceutical compositions include, without limitation, a pharmaceutically acceptable polar aprotic solvent, a pharmaceutically acceptable polar protic solvent and a pharmaceutically acceptable non-polar solvent. A pharmaceutically acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically acceptable non-polar solvent includes, without limitation, pentane, cyclopentane, hexane, cyclohexane, benzene, toluene, 1,4-dioxane, chloroform, n-methyl-pyrrolidone (NMP), and diethyl ether.

The method of administration as well as the dosage range which are suitable in a specific case depend on the species to be treated and on the state of the respective condition or disease, and may be optimized using techniques known in the art. Most often, the daily dose of active compound in a patient may range from 0.0005 mg to 15 mg per kg, more usually 0.001 mg to 7.5 mg per kg. Dosing can be single dosage or cumulative (serial dosing), and can be readily determined by one skilled in the art. For instance, treatment may comprise a one-time administration of an effective dose of a pharmaceutical composition as disclosed herein. Alternatively, treatment may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Pharmaceutical compositions may contain any conventional non-toxic pharmaceutically acceptable carriers, adjuvants or vehicles. In some cases, the pH of the formulation may be adjusted with acceptable pharmaceutical or food grade acids, bases or buffers to enhance the stability of the formulated composition or its delivery form.

Liquid dosage forms for oral administration include acceptable pharmaceutical or food grade emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylsulfoxide (DMSO) dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, lozenges, pills, powders, and granules. In such solid dosage forms, the active compound is mixed with at least one inert, acceptable pharmaceutical or food grade excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agaragar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof, and j) sweetening, flavoring, perfuming agents, and mixtures thereof. In the case of capsules, lozenges, tablets and pills, the dosage form may also comprise buffering agents.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed or extended manner. Examples of embedding compositions which can be used include polymeric substances and waxes. Tablet formulations for extended release are also described in U.S. Pat. No. 5,942,244.

Compositions may contain a compound as disclosed herein, alone or with other therapeutic compound(s). A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g., a hydrochloride. Additionally, therapeutic compound disclosed herein may be provided as racemates, or as individual enantiomers, including an R- or S-enantiomer. Thus, the therapeutic compound disclosed herein may comprise an R-enantiomer only, a S-enantiomer only, or a combination of both an R-enantiomer and a S-enantiomer of a therapeutic compound. In some aspects, the therapeutic compound may have anti-inflammatory activity, such as a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, aceclofenac, acemetacin, actarit, alcofenac, alminoprofen, amfenac, aloxipirin, aminophenazone, antraphenine, aspirin, azapropazone, benorilate, benoxaprofen, benzydamine, butibufen, celecoxib, chlorthenoxacin, choline salicylate, clometacin, dexketoprofen, diclofenac, diflunisal, emorfazone, epirizole; etodolac, etoricoxib, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, lumiracoxib, mefenamic acid, meloxicam, metamizole, metiazinic acid, mofebutazone, mofezolac, nabumetone, naproxen, nifenazone, niflumic acid, oxametacin, phenacetin, pipebuzone, pranoprofen, propyphenazone, proquazone, protizinic acid, rofecoxib, salicylamide, salsalate, sulindac, suprofen, tiaramide, tinoridine, tolfenamic acid, valdecoxib, and zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase-1 (COX-1) inhibitor, and a selective cyclooxygenase-2 (COX-2) inhibitor. An NSAID may be a profen. Examples of a suitable salicylate derivative NSAID include, without limitation, acetylsalicylic acid (aspirin), diflunisal, and salsalate. Examples of a suitable p-amino phenol derivative NSAID include, without limitation, paracetamol and phenacetin. Examples of a suitable propionic acid derivative NSAID include, without limitation, alminoprofen, benoxaprofen, dexketoprofen, fenoprofen, flurbiprofen, ibuprofen, indoprofen, ketoprofen, loxoprofen, naproxen, oxaprozin, pranoprofen, and suprofen. Examples of a suitable acetic acid derivative NSAID include, without limitation, aceclofenac, acemetacin, actarit, alcofenac, amfenac, clometacin, diclofenac, etodolac, felbinac, fenclofenac, indometacin, ketorolac, metiazinic acid, mofezolac, nabumetone, naproxen, oxametacin, sulindac, and zomepirac. Examples of a suitable enolic acid (oxicam) derivative NSAID include, without limitation, droxicam, isoxicam, lornoxicam, meloxicam, piroxicam, and tenoxicam. Examples of a suitable fenamic acid derivative NSAID include, without limitation, flufenamic acid, mefenamic acid, meclofenamic acid, and tolfenamic acid. Examples of a suitable selective COX-2 inhibitors include, without limitation, celecoxib, etoricoxib, firocoxib, lumiracoxib, meloxicam, parecoxib, rofecoxib, and valdecoxib.

The following examples show illustrative aspects of the disclosure and should not be construed as limiting the scope of the invention.

Example 1

This example illustrates the synthesis of a compound having the structure:

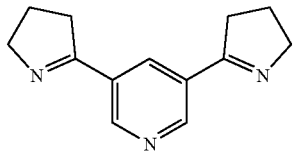 [SMILES: c1ncc(C2=NCCC2)cc1C1=NCCC1]

Figure 2:
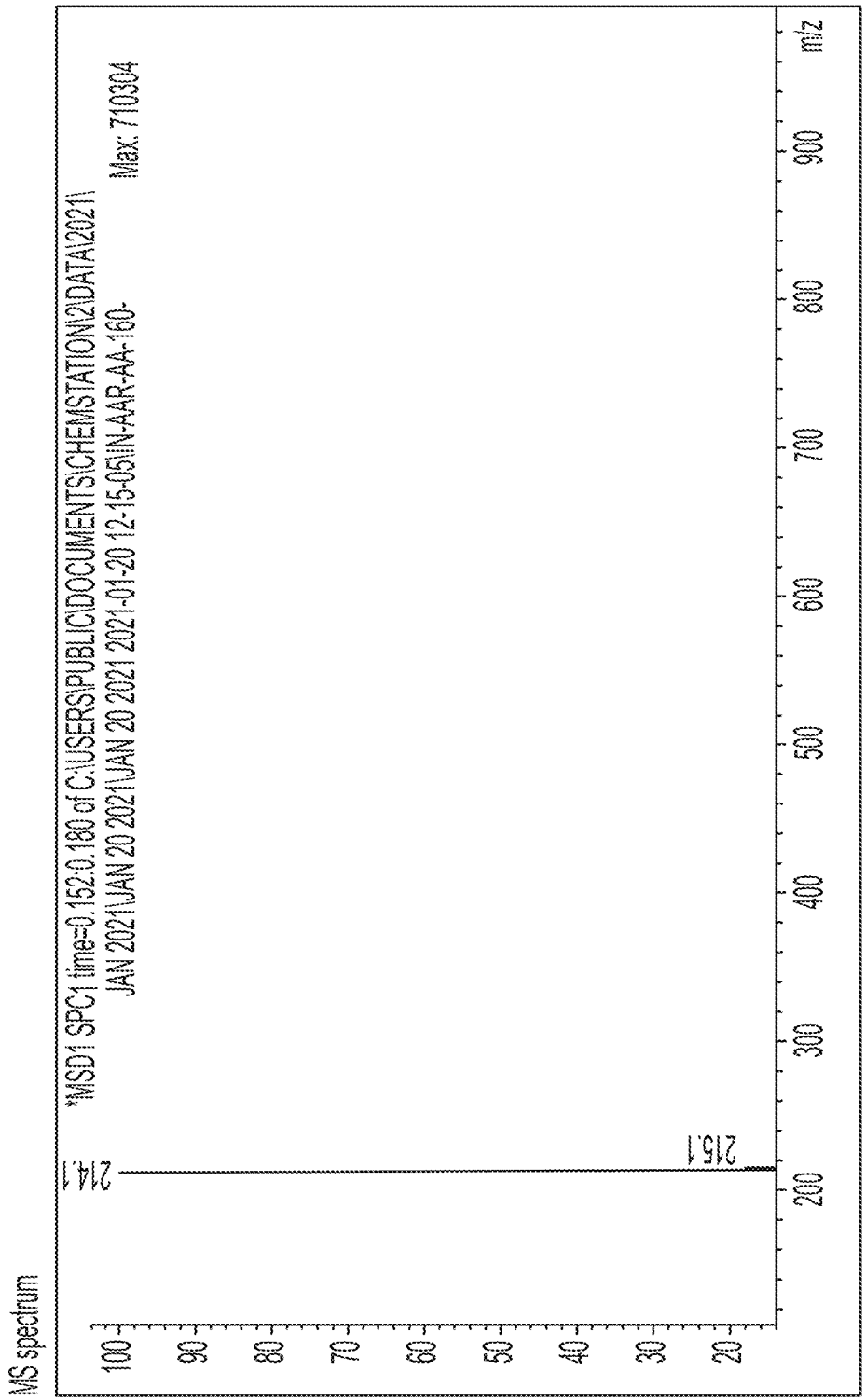
FIG. 2 is a mass spectrum for the compound whose NMR spectrum is shown in FIG. 1.
Figure 3:
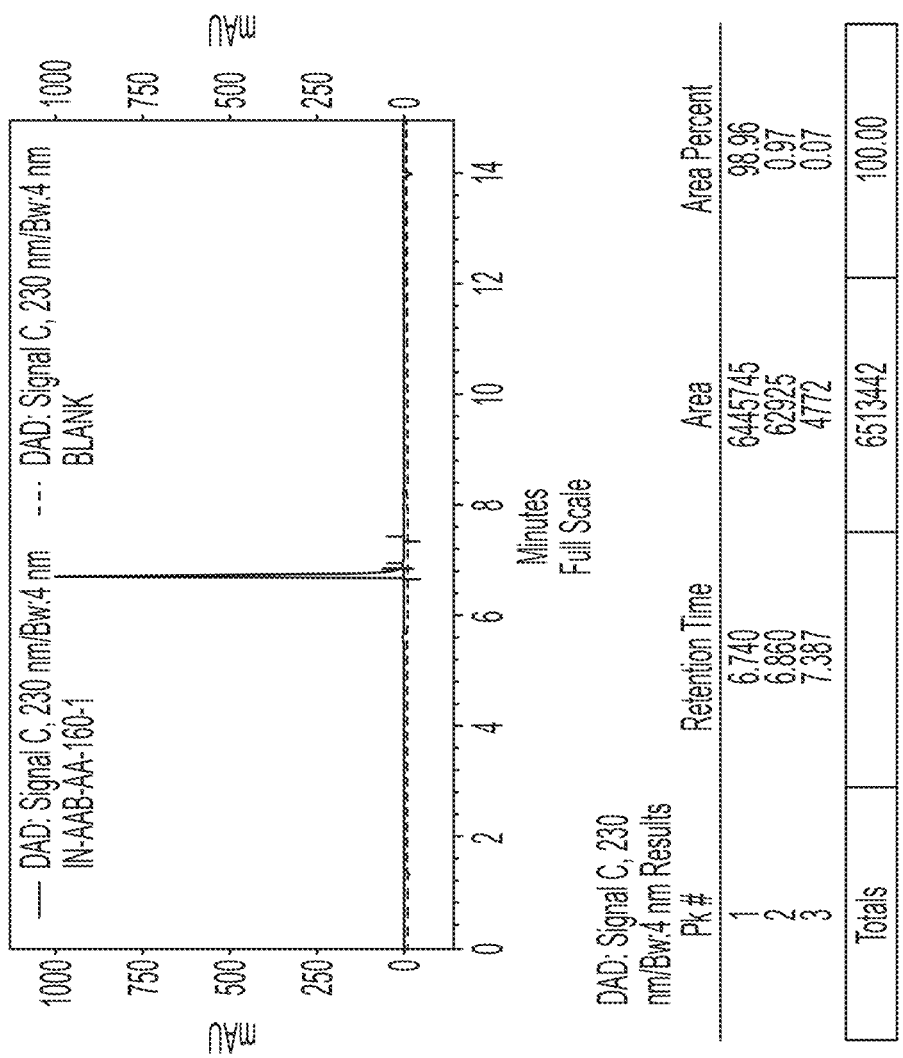
FIG. 3 is a high-performance liquid chromatogram (HPLC) for the compound whose NMR spectrum is shown in FIG. 1.

The above-depicted compound was prepared according to the following synthesis pathway. Each of the starting reagents shown is commercially available from various chemical suppliers. The attributes of the synthesis product are summarized in Table 1 below. The NMR spectrum, mass spectrum, and HPLC for the compound are presented in FIGS. 1-3, respectively.

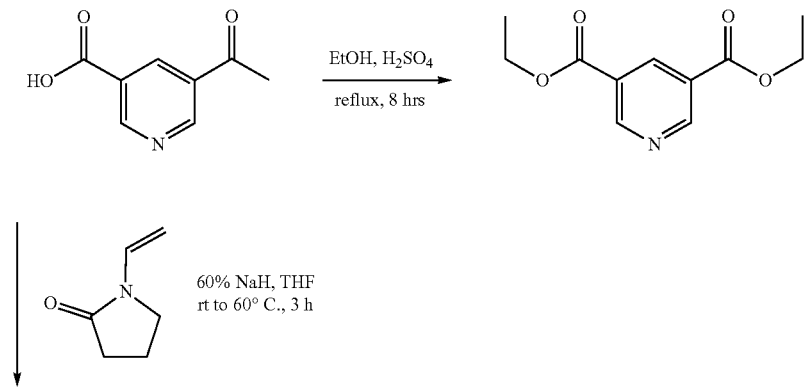

-continued

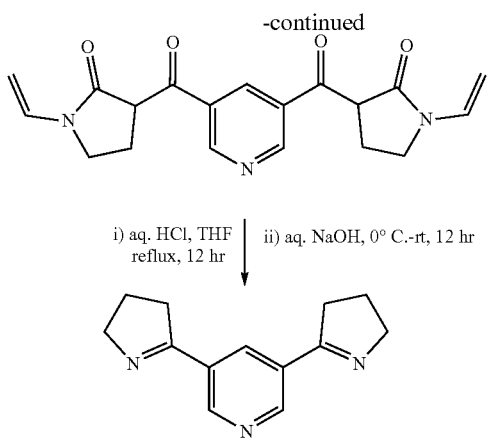

i) aq. HCl, THF reflux, 12 hr    ii) aq. NaOH, 0° C.-rt, 12 hr

TABLE 1

| Test | Result/Reference | See FIG. |
|---|---|---|
| Appearance | Off-white solid | N/A |
| NMR spectrum | $^1$H NMR, 400 MHZ, dimethyl sulfoxide-d6, consistent | 1 |
| Mass spectrum | ESI (multimode), m/z 214.1 [M + H]$^+$ | 2 |
| HPLC | 98.9% (area%), Eclipse plus C18, 100 × 4.6 mm, 3.5 μm UV 230 nm Detection | 3 |

Example 2

This example describes testing the compound prepared in Example 1 in the BioMAP Diversity PLUS (Eurofins Discovery, Burlingame, California) panel of 12 human primary cell-based systems designed to model different aspects of the human body in an in vitro format. The 12 systems in the Diversity PLUS panel allow test agent characterization in an unbiased way across a broad set of systems modeling various human disease states. BioMAP systems are constructed with one or more primary cell types from healthy human donors, with stimuli (such as cytokines or growth factors) added to capture relevant signaling networks that naturally occur in human tissue or pathological conditions. Vascular biology is modeled in both a Th1 (3C system) and a Th2 (4H system) inflammatory environment, as well as in a Th1 inflammatory state specific to arterial smooth muscle cells (CASM3C system). Additional systems recapitulate aspects of the systemic immune response including monocyte-driven Th1 inflammation (LPS system) or T cell stimulation (SAg system), chronic Th1 inflammation driven by macrophage activation (lMphg system) and the T cell-dependent activation of B cells that occurs in germinal centers (BT system). The BE3C system (Th1) and the BF4T system (Th2) represent airway inflammation of the lung, while the MyoF system models myofibroblast-lung tissue remodeling. Lastly, skin biology is addressed in the KF3CT system modeling Th1 cutaneous inflammation and the HDF3CGF system modeling wound healing.

Figure 4:
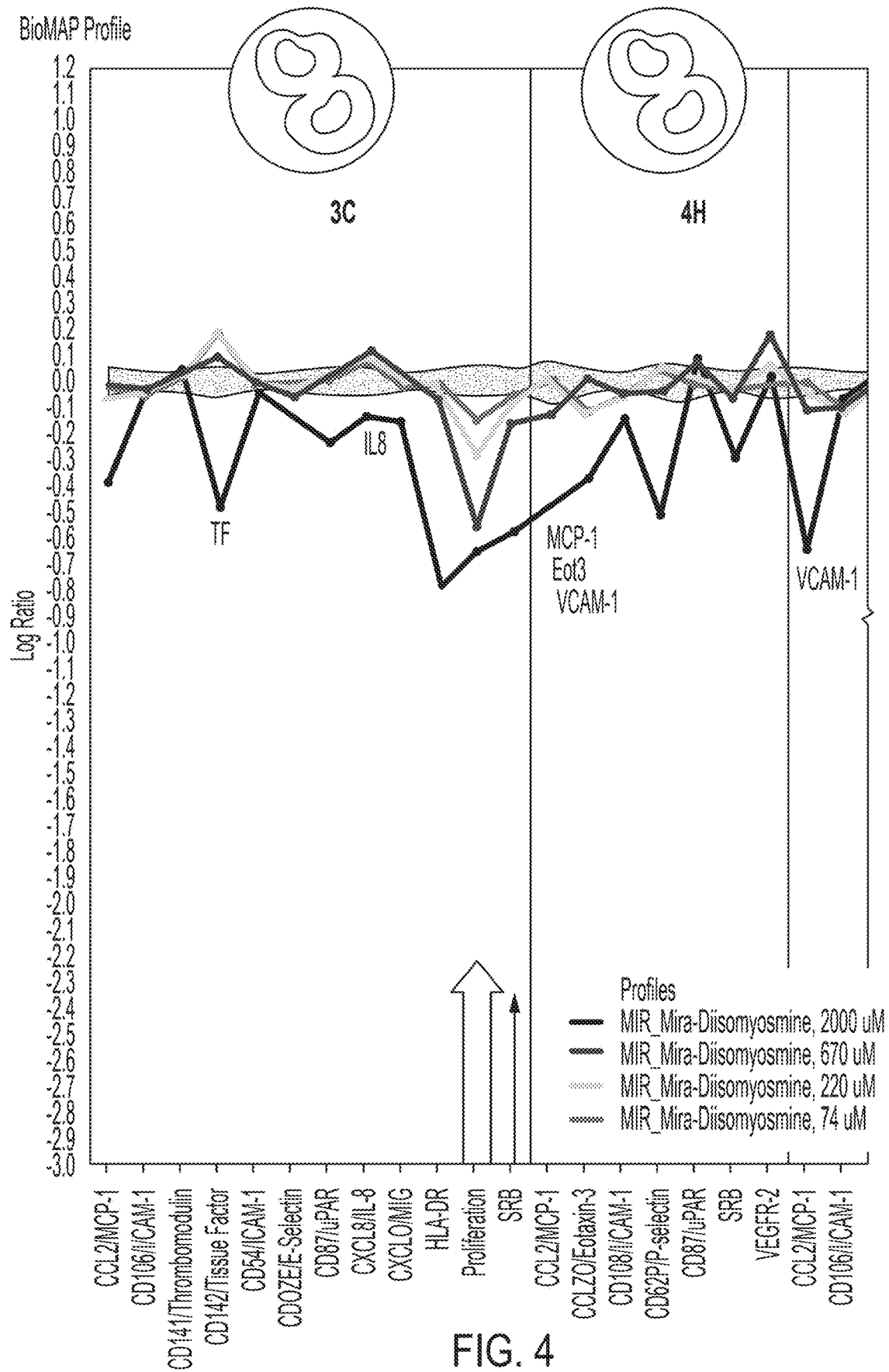
FIG. 4 is the Diversity PLUS Panel profile for the compound whose NMR spectrum is shown in FIG. 1.
Figure 4:
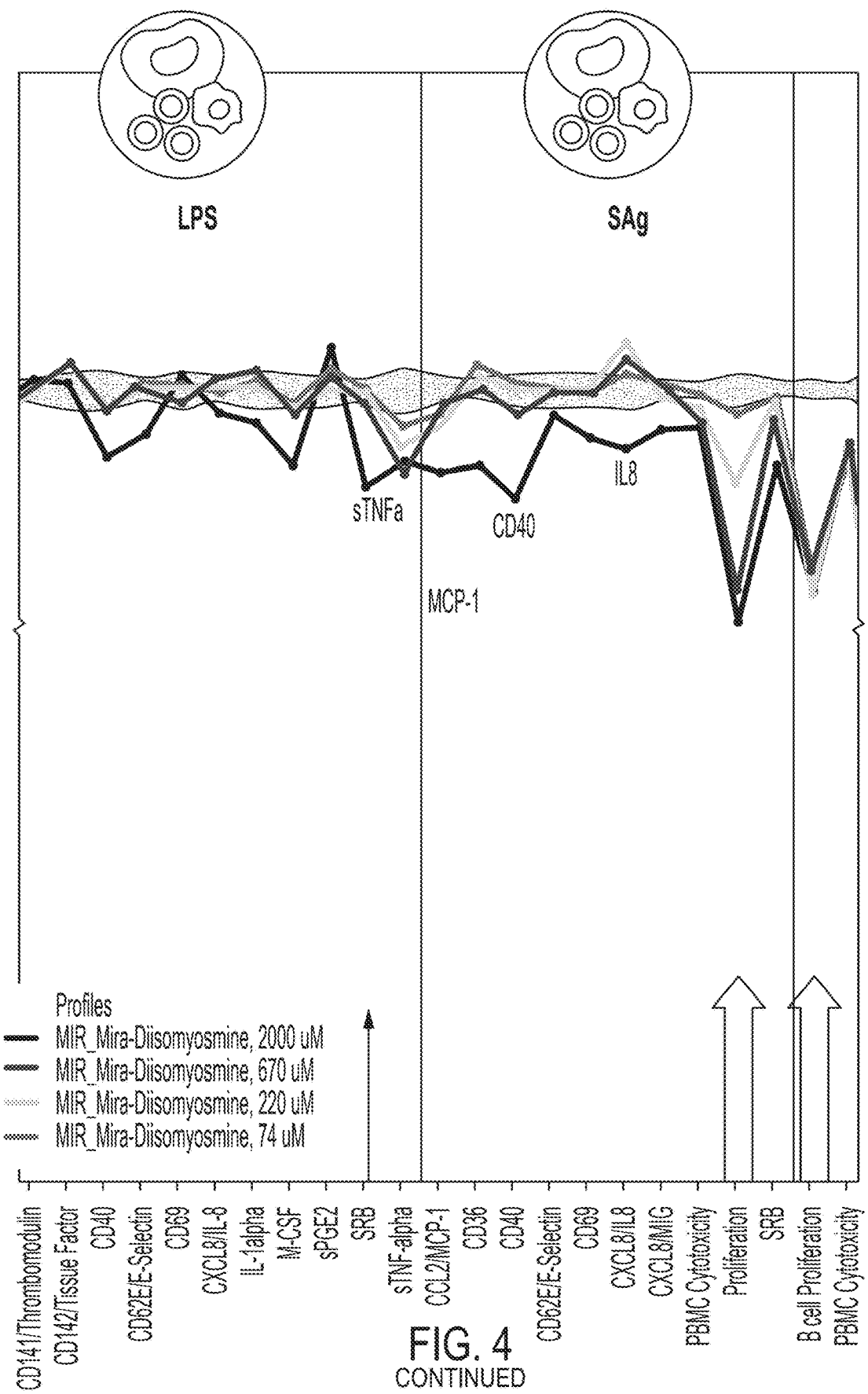
Figure 4:
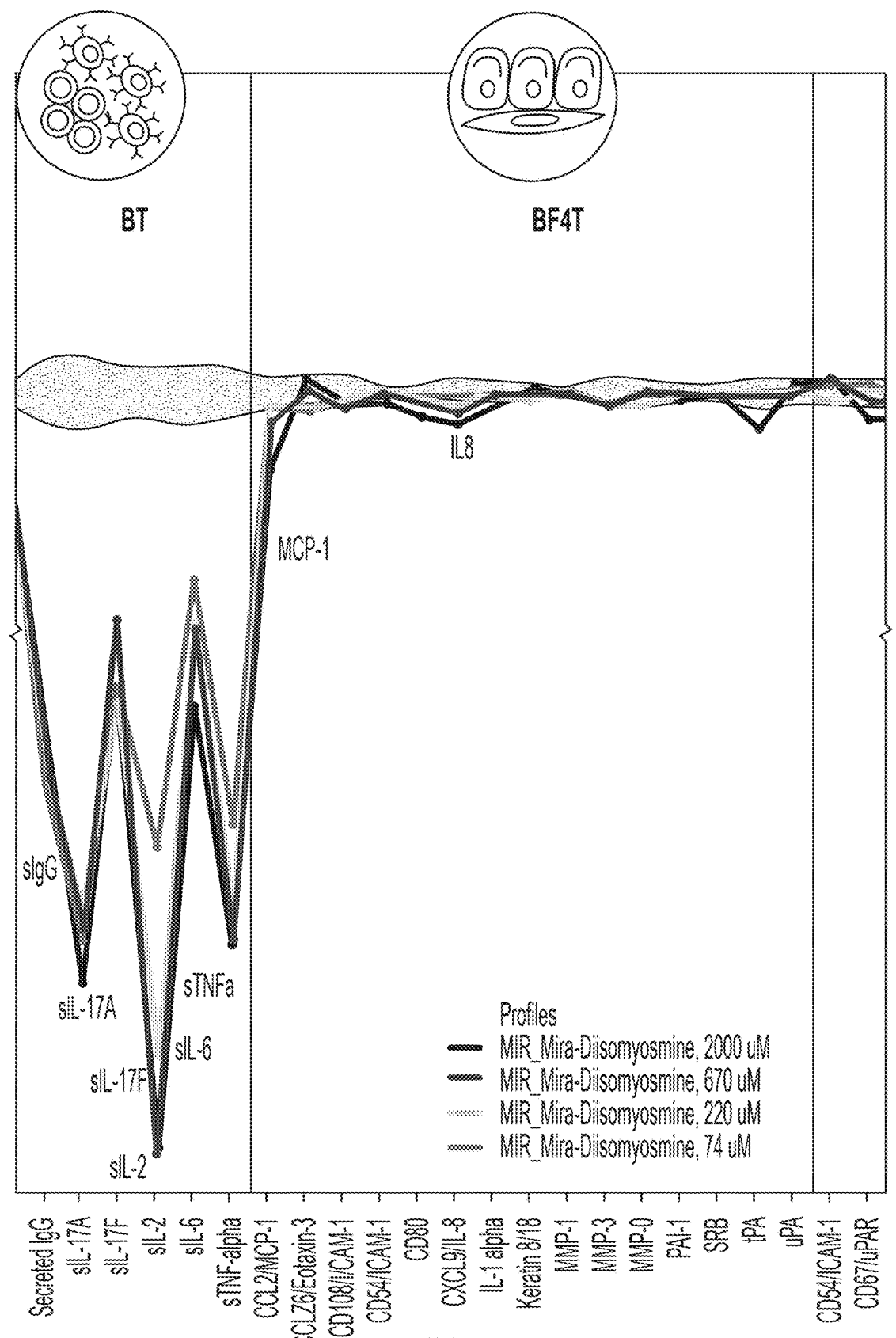
Figure 4:
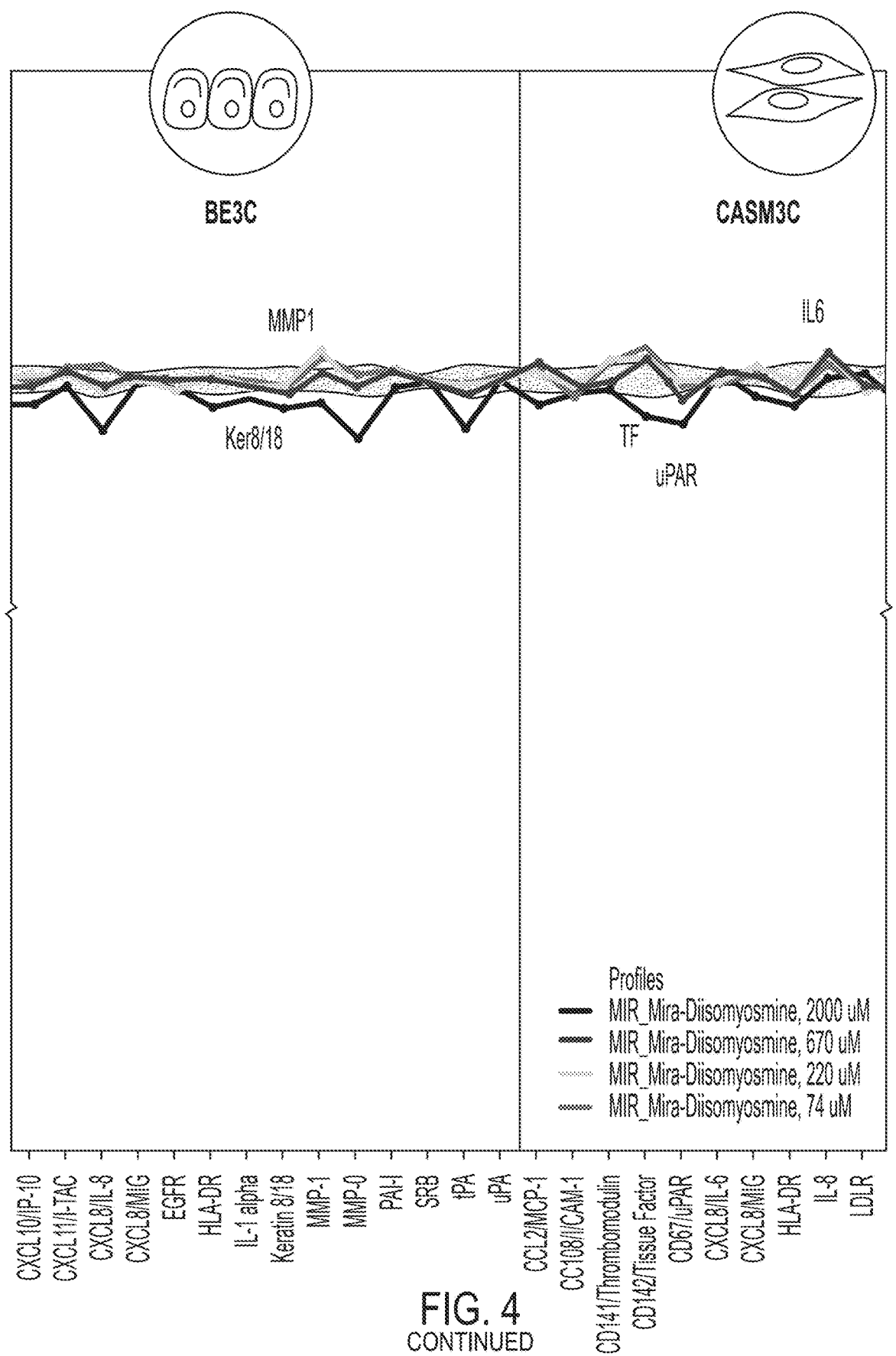
Figure 4:
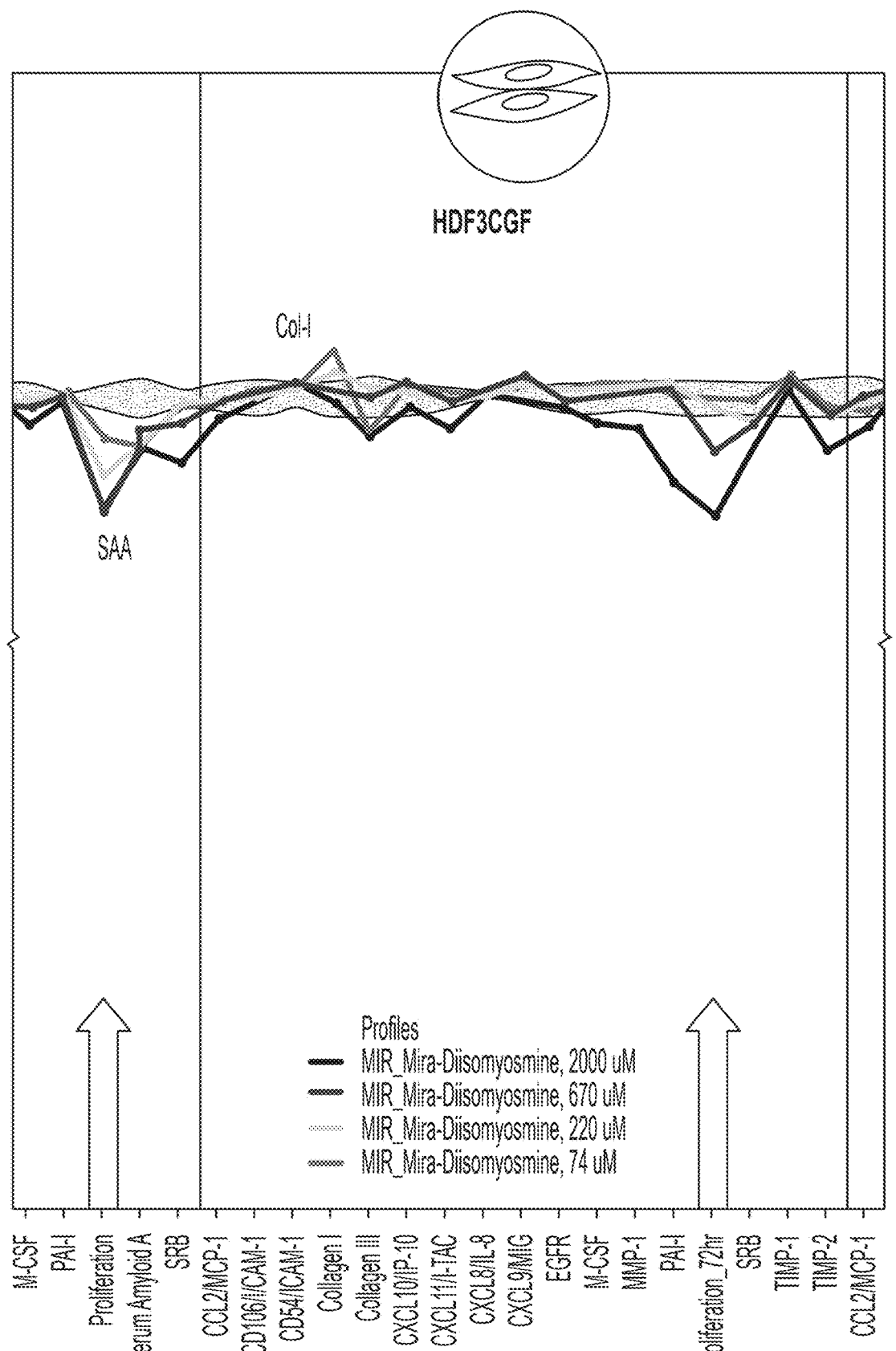
Figure 4:
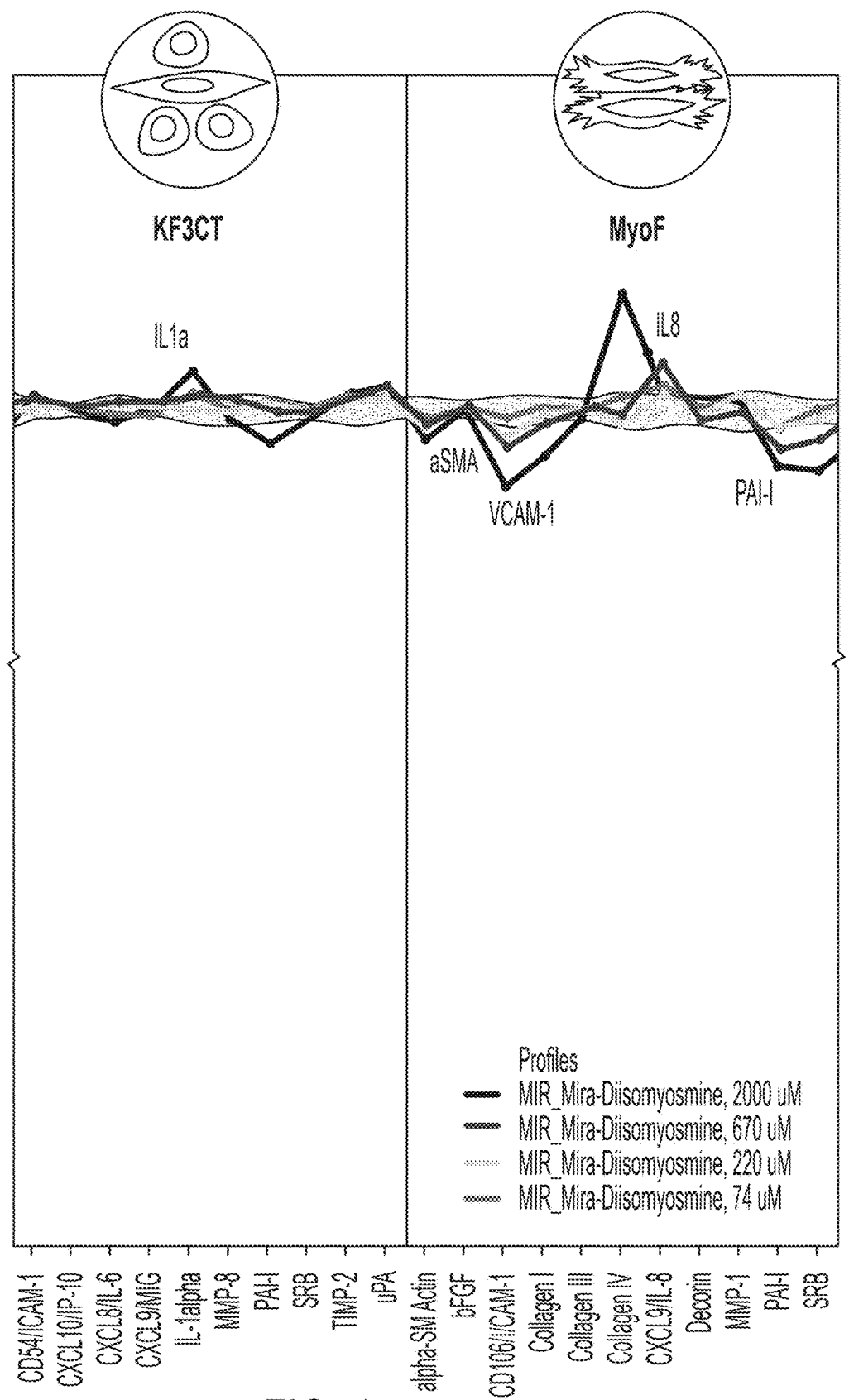
Figure 4:
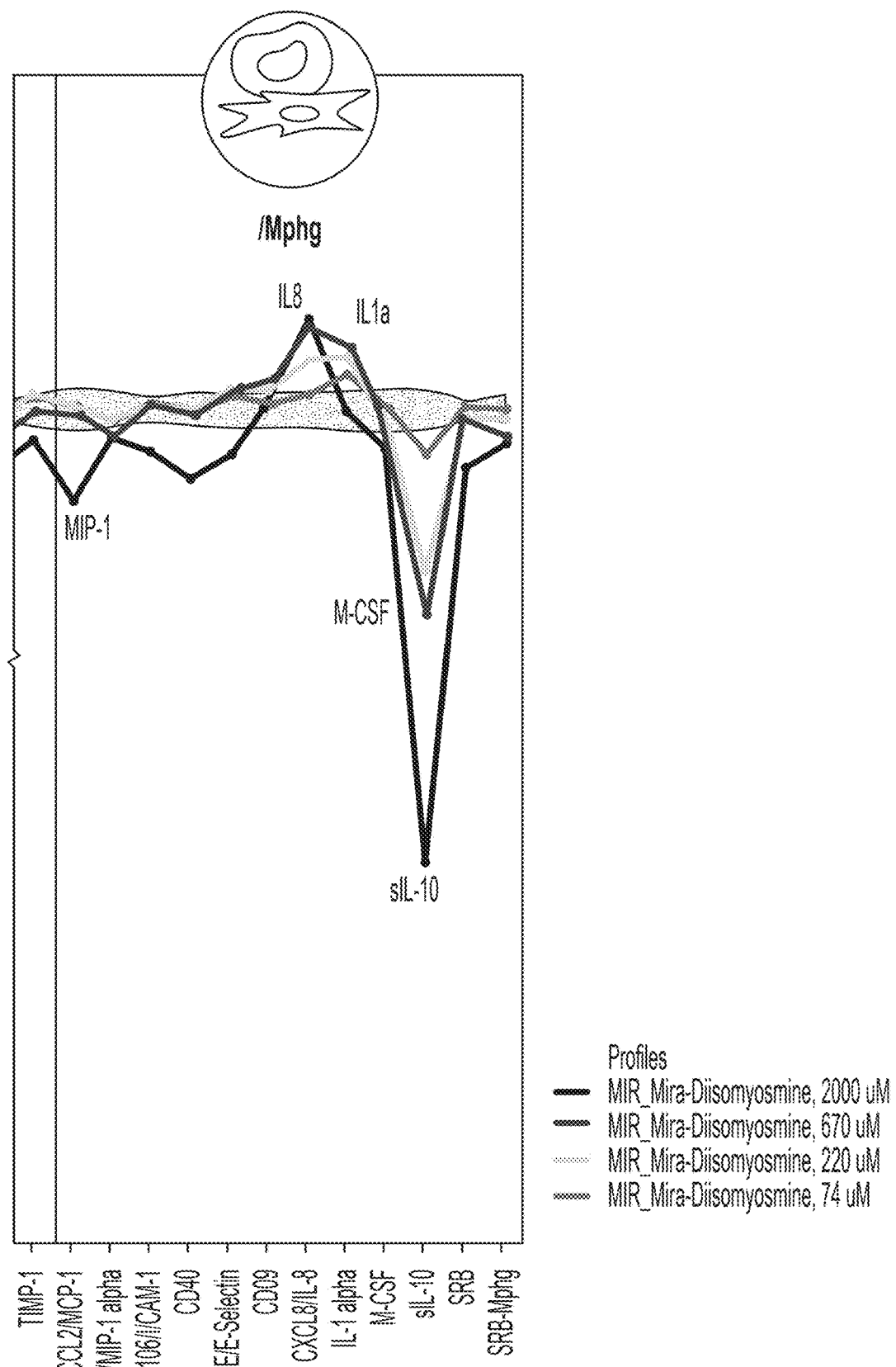

FIG. 4 shows the Diversity PLUS Panel profile. The X-axis lists the quantitative protein-based biomarker readouts measured in each system. The Y-axis represents a log-transformed ratio of the biomarker readouts for the drug-treated sample (n=1) over vehicle controls (n≥6). The grey region around the Y-axis represents the 95% significance envelope generated from historical vehicle controls. Biomarker activities are annotated when two or more consecutive concentrations change in the same direction relative to vehicle controls, are outside of the significance envelope, and have at least one concentration with an effect size >20% (|log 10 ratio|>0.1). Biomarker key activities are described as modulated if these activities increase in some systems, but decrease in others. Cytotoxicity is indicated on the profile plot by a thin black arrow above the X-axis, and antiproliferative effects are indicated by a thick grey arrow. Cytotoxicity and antiproliferative arrows only require one concentration to meet the indicated threshold for profile annotation. As summarized in Table 2 below, the compound was active with 35 annotated readouts. Specifically, the compound impacted inflammation-related activities (decreased Eotaxin 3, VCAM-1, MCP-1, SAA, sTNFα, MIP-1α; increased IL-1α, IL-6; modulated IL-8), immunomodulatory activities (decreased CD40, sIL-1β, sIgG, M-CSF, sIL-17A, sIL-6, sIL-17F, sIL-2), tissue remodeling activities (decreased PAI-1, uPAR, αSMA, Keratin 8/18; increased collagen I, MMP-1), and hemostasis-related activities (increased TF).

TABLE 2

| Biological Disease Category | Decreased Activity | Increased Activity | Modulated Activity |
|---|---|---|---|
| Inflammation-related activities | MIP-1, sTNFα, VCAM-1, SAA, MCP-1, Eot3 | IL1a, IL6 | IL8 |
| Immunomodulatory activities | M-CSF, sigG, sIL-10, sIL-2, sIL-6, CD40, SIL-17A, SIL-17F | | |
| Tissue remodeling activities | uPAR, aSMA, PAI-1, Ker8-18 | MMP1, Col-1 | |
| Hemostasis-related activities | | TF | |

At concentrations not associated with cytotoxicity, the compound was antiproliferative to human primary endothelial cells (670 μM, 220 μM, 74 μM), T cells (670 μM, 220 μM), B cells (670 μM, 220 μM, 74 μM), coronary artery smooth muscle cells (670 μM, 220 μM, 74 μM), and fibroblasts (670 μM).

At the lower three concentrations tested, the compound was active with 23 annotated readouts. The compound impacted inflammation-related activities (decreased Eotaxin 3, VCAM-1, MCP-1, SAA, sTNFα; increased IL-8, IL-1α, IL-6), immunomodulatory activities (decreased sIL-1β, sIgG, sIL-17A, sIL-6, sIL-17F, sIL-2), tissue remodeling activities (decreased PAI-1; increased collagen I, MMP-1), and hemostasis-related activities (increased TF).

Significantly, the compound of Example 1 simultaneously inhibited the soluble forms of TNF-α, IL-6 and IL-17, and was antiproliferative to the human primary cell types: T cells, B cells, fibroblasts, and endothelial cells. TNF-α is an initiator of the acute phase pro-inflammatory cytokines. A therapeutic example of a TNF-α inhibitor is adalimumab (Humira®). IL-6 is activated by TNF-α in pro-inflammatory cascade. It is a primary cytokine implicated in depression. A therapeutic example of an IL-6 inhibitor is tocilizumab (Actemra®). IL-17 plays a key role in the pathogenesis of various autoimmune disorders. A therapeutic example of an IL-17 inhibitor is secukinumab (Cosentyx®).

A table of the top three similarity matches (see Table 3 below) from an unsupervised search of the BioMAP Reference Database of >4,500 agents showed that the compound of Example 1 (2000 μM) is most similar to cetylpyridinium chloride (1.1 μM) (Pearson's correlation coefficient, r=0.878). The Pearson's correlation coefficient between these two profiles is above the determined threshold of r=0.7, indicating these compounds share mechanistically relevant similarity. Cetylpyridinium chloride is a cationic quaternary ammonium compound that is used as an antiseptic in commercial products. Cetylpyridinium is a drug excipient with off target activities as reported using the BioMAP Diversity PLUS Panel with Toxicity Signature Analysis (Science, 2020; https://doi.org/10.1126/science.aaz9906).

There are 18 common activities that are annotated within the following systems: SAg (CD40, CD69, Pcyto, Prolif), BT (Prolif, sIgG, sIL-17A, sIL-17F, sIL-2, sIL-6, sTNFα), CASM3C (Prolif), HDF3CGF (Collagen III, Prolif 72), MyoF (Collagen IV), and lMphg (E-selectin, sIL-1β, SRB-M).

Figure 5:
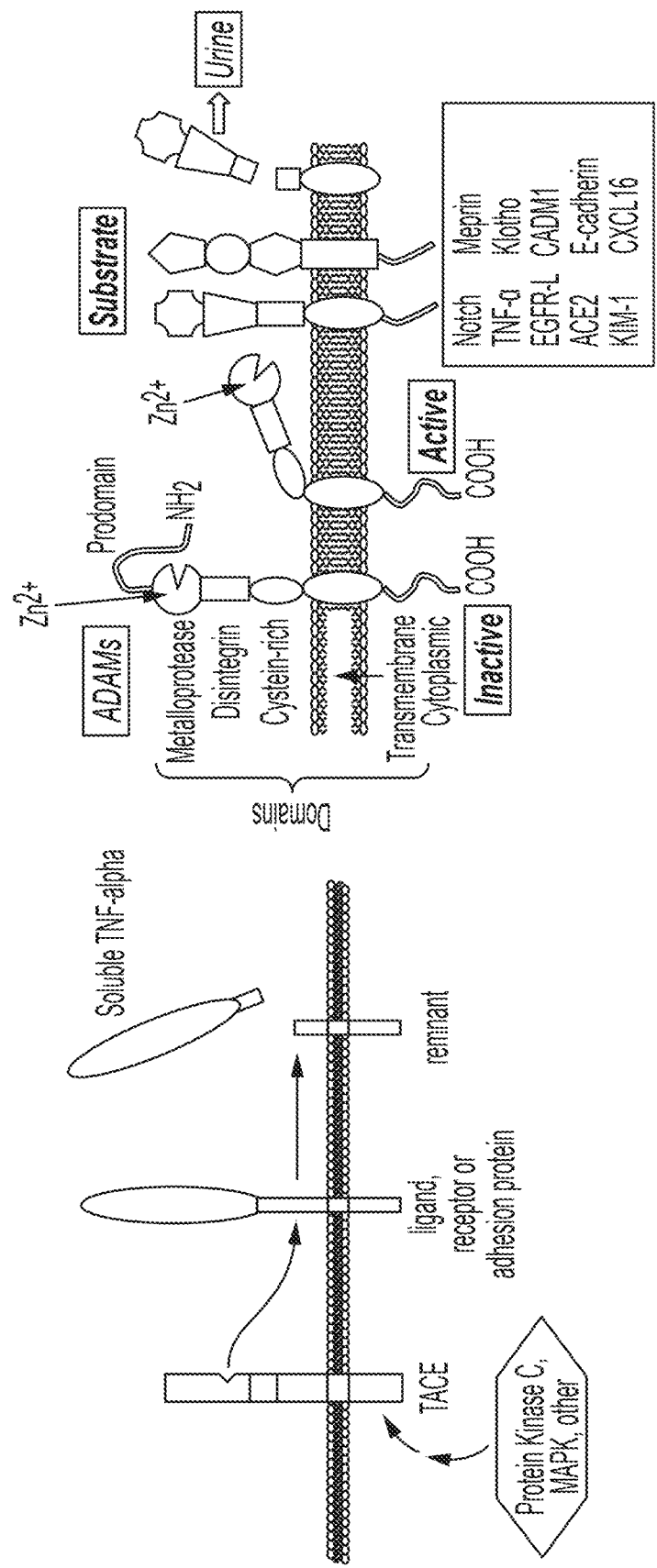
FIG. 5 illustrates the TNF-α converting enzyme (TACE), a metalloprotease that requires $Zn^{2+}$ and cleaves TNF-α, IL-6 and IL-17 into their soluble forms.
Figure 6:
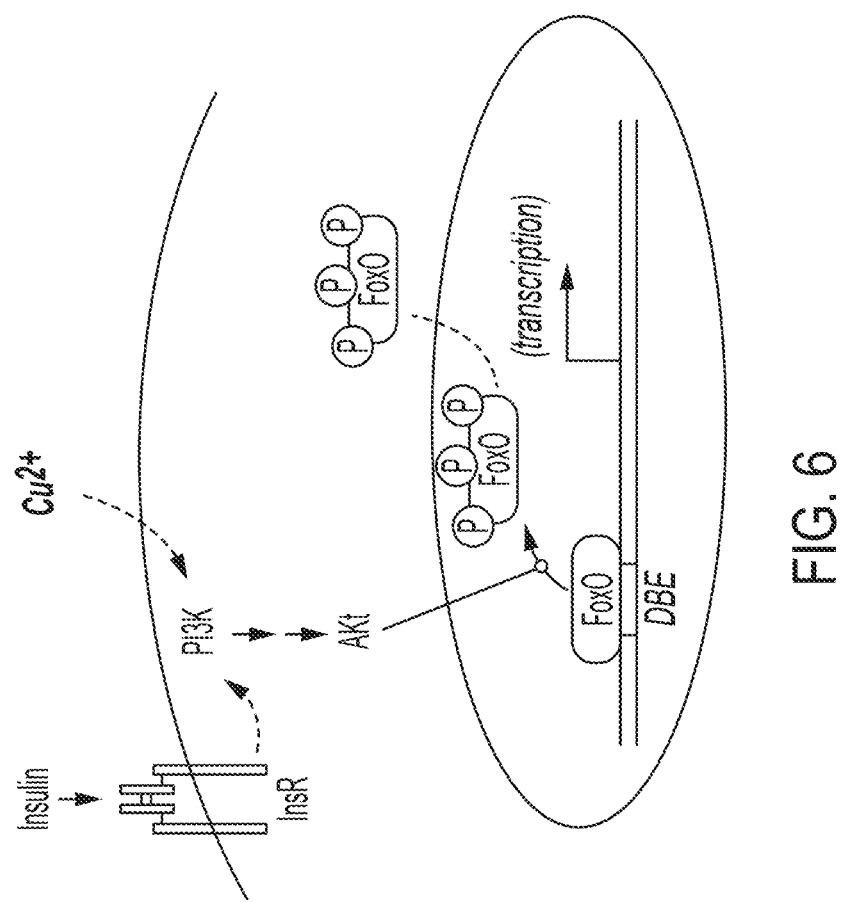
FIG. 6 illustrates phosphoinositide 3-kinase (PI3K) activated in cells exposed to insulin via the insulin receptor (InsR); $Cu^{2+}$ and $Zn^{2+}$ (not illustrated) stimulate PI3K as well as PI3K-dependent activation of the Ser/Thr kinase Akt.

The pattern of protein inhibition and stimulation appeared most similar to PI3K, which are $Zn^{2+}$ and $Cu^{2+}$ stimulated. This implies that chelation of Cu and Zn inhibits PI3K. It follows that the compound of Example 1 inhibits the TNF-α converting enzyme (TACE, also called ADAM-17), a metalloprotease that cleaves TNF-α, IL-6 and IL-17 into their soluble forms, as schematically shown in FIG. 5. Phosphoinositide 3-kinase (PI3K) is activated in cells exposed to insulin via the insulin receptor (InsR). $Cu^{2+}$ and $Zn^{2+}$ (not illustrated) stimulate PI3K as well as PI3K-dependent activation of the Ser/Thr kinase Akt, as schematically shown in FIG. 6.

Therapeutic examples of PI3K inhibitors include idelalisib (Zydelig®), a drug used to treat certain blood cancers. The substance blocks P1106, the delta isoform of the enzyme phosphoinositide 3-kinase. Also, Novartis has a Phase III Study of a PI3K inhibitor, BKM120/Placebo With Fulvestrant in Postmenopausal Patients With Hormone Receptor Positive HER2-negative Locally Advanced or Metastatic Breast Cancer Refractory to Aromatase Inhibitor (BELLE-2).

TABLE 3

| Example 1 concentration | Database match | BioMAP Z-standard | Pearson's score | #common on readout | Mechanism class |
|---|---|---|---|---|---|
| 74 μM | GDC0941, 370 nM | 21.6 | 0.946 | 148 | PI3K inhibitor |

TABLE 3-continued

| Example 1 concentration | Database match | BioMAP Z-standard | Pearson's score | #common on readout | Mechanism class |
|---|---|---|---|---|---|
| | Cetylpyridin chloride, 1 μM | 21.119 | 0.942 | 148 | Antiseptic agent |
| | Idelalisib, 1 μM | 20.258 | 0.933 | 148 | PI3K-delta inhibitor |

Example 3

Analysis of 3,5-bis(3,4-dihydro-2H-pyrrol-2-yl)pyridine using the BioMAP® system. The compound used in Example 3 has the structure:

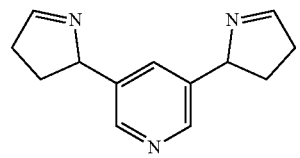 [SMILES: C1=NC(c2cncc(C3CCC=N3)c2)CC1]

In this Example, the BioMAP® system was used to test safety, efficacy and function of 3,5-bis(3,4-dihydro-2H-pyrrol-2-yl)pyridine in models of human tissue and disease biology of the vasculature, skin, lung, and inflammatory tissues.

Example 3.1: Description of the BioMap® System Used in this Example

BioMAP® panels consist of human primary cell-based systems designed to model different aspects of the human body in an in vitro format. BioMAP® systems are constructed with one or more primary cell types from healthy human donors, with stimuli (such as cytokines or growth factors) added to capture relevant signaling networks that naturally occur in human tissue or pathological conditions. Vascular biology is modeled in both a Th1 (3C system) and a Th2 (4H system) inflammatory environment, as well as in a Th1 inflammatory state specific to arterial smooth muscle cells (CASM3C system). Additional systems recapitulate aspects of the systemic immune response including monocyte-driven Th1 inflammation (LPS system) or T cell stimulation (SAg system), chronic Th1 inflammation driven by macrophage activation (Mphg system) and the T cell-dependent activation of B cells that occurs in germinal centers (BT system). The BE3C system (Th1) and the BF4T system (Th2) represent airway inflammation of the lung, while the MyoF system models myofibroblast-lung tissue remodeling. Lastly, skin biology is addressed in the KF3CT system modeling Th1 cutaneous inflammation and the HDF3CGF system modeling wound healing. A subset of 8 of these BioMAP systems has previously been used in the U.S. Environmental Protection Agency (EPA)'s ToxCast™ program to characterize environmental chemicals, define mechanisms of toxicity and to develop predictive signatures of toxicity.

The diseases and conditions modeled by the above cellular systems are shown in Table 4 below.

TABLE 4 overview of disease models

| System name | Modeled Diseases and conditions |
|---|---|
| 3C | Th1 type vascular inflammation diseases or conditions such as chronic inflammatory diseases, vascular inflammation, and restenosis. |
| 4H | Th2 type vascular inflammation diseases or conditions such as allergy, asthma and ulcerative colitis. |
| LPS | Diseases and conditions related to Th1 type chronic inflammation and monocyte activation responses such as atherosclerosis, restenosis, rheumatoid arthritis, and metabolic disease. |
| SAg | Diseases and conditions related to Th1 type chronic inflammation and T cell effector responses in the context of the vascular endothelium. In particular, inflammation driven conditions such as organ transplantation related responses, rheumatoid arthritis, psoriasis, Crohn's disease and hematological oncology. |
| BT | Diseases and conditions related to T cell dependent B cell proliferation, activation, and class switching in the germinal centers of secondary lymphoid organs, and related conditions such as systemic lupus erythematosus (SLE), hematological oncology, autoimmune indications, asthma and allergy. |
| BF4T | Th2 type lung inflammation such as asthma, pulmonary fibrosis, and Chronic Obstructive Pulmonary Disease (COPD) exacerbations. |
| BE3C | Th1 type lung inflammation such as sarcoidosis and pulmonary responses to respiratory infections. |
| CASM3C | Th1 type vascular inflammation such as chronic inflammatory diseases, vascular inflammation, and restenosis. |
| HDF3CGF | Th1 type inflammation such as fibrosis, rheumatoid arthritis, and psoriasis. HDF3CGF is also a model for stromal biology in tumors. |
| KF3CT | Th1 type cutaneous inflammation responses to mechanical, chemical, or infectious agents, and psoriasis and dermatitis. |
| MyoF | Multiple fibrosis diseases or inflammation related responses in fibrotic tissue. |
| /Mphg | Th1 type chronic inflammation and macrophage activation responses such as atherosclerosis, restenosis, rheumatoid arthritis, and other chronic inflammatory diseases. |

Table 5 provides further description of the above described markers and associated BioMAP® systems.

TABLE 5

Markers identified in BioMAP ® profile of the test agents.

| Marker | System name | Description/full name | Alternative name |
|---|---|---|---|
| Eotaxin 3 | 4H | chemokine | CCL26 |
| MCP-1 | 4H | chemoattractant | CCL2 |
| MIP-1α | | Macrophage Inflammatory Proteins (MIP) | |
| I-TAC | BE3C | Interferon-inducible T call alpha chemoattractant | CXCL11 |
| VCAM-1 | /Mphg | Vascular Cell Adhesion Molecule 1 | CD106 |
| SAA | CASM3C | Serum Amyloid A | |
| MIG | 3C | Monokine induced by gamma interferon | CXCL9 |
| IP-10 | KF3CT | Interferon gamma inducible protein 10 | CXCL10 |
| IL-6 | CASM3C | Interleukin-6 | |
| IL-1α | BE3C | Interleukin-1 alpha | |
| P-selectin | 4H | Cell-adhesion molecule | CD62P |
| sPGE2 | LPS | Prostaglandin E2 | |
| STNFα | LPS | Tumor necrosis factor alpha | |
| IL-8 | LPS | Interleukin-8 | CXCL8 |
| CD40 | LPS | Cell surface adhesion molecule | |
| SIL-10 | /Mphg | Interleukin-10 | |
| sIgG | BT | Secreted immunoglobulin G | |
| HLA-DR | CASM3C | Cell surface heterodimer involved in antigen presentation | |
| SIL-17A | BT | Interleukin 17A | |
| CD38 | SAg | T cell activation marker | |
| SIL-17F | BT | Interleukin 17F | |
| SIL-2 | BT | Interleukin 2 | |
| CD69 | SAg | Cell surface activation antigen | |
| TIMP-1 | HDF3CGF | Tissue inhibitor of matrix metallprotease-7 | |
| Collagen I | HDF3CGF/MyoF | Fibrillar collagen of skin, bone, tendons and other connective tissue. | |
| Collagen IV | MyoF | Major structural component of basal lamina. | |
| Collagen III | HDF3CGF/MyoF | Extensible collage in skin, lung, and vascular system. | |
| MMP-1 | MyoF/BE3C | Matrix-metalloproteinase 1 | |
| PAI-1 | MyoF | Plasminogen activator inhibitor-1 | |
| uPAR | 3C | Urokinase plasminogen activator receptor | CD87 |
| aSMA | MyoF | Alpha-smooth muscle actin | |
| bFGF | MyoF | Basic fibroblast growth factor | |
| Ker8/18 | BF4T/BE3C | Keratin 8/18 | |
| MMP-9 | BF4T/BE3C | Matrix-metalloproteinase 9 | |
| TM | LPS | TM is thrombomodulin | |
| TF | LPS | TF is Tissue Factor | |

TABLE 5-continued

Markers identified in BioMAP® profile of the test agents.

| Marker | System name | Description/full name | Alternative name |
|---|---|---|---|
| LDLR | BE3C | low-density lipoprotein receptor | |

Each test agent subjected to tested in BioMAP® generates a signature BioMAP® profile that is created from the changes in protein biomarker readouts within individual system environments. Biomarker readouts (7-17 per system) are selected for therapeutic and biological relevance, are predictive for disease outcomes or specific drug effects and are validated using agents with known mechanism of action (MoA). Each readout is measured quantitatively by immune-based methods that detect protein (e.g., ELISA) or functional assays that measure proliferation and viability. BioMAP® readouts are diverse and include cell surface receptors, cytokines, chemokines, matrix molecules and enzymes. In total, the Diversity PLUS panel contains 148 biomarker readouts that capture biological changes that occur within the physiological context of the particular BioMAP® system.

Using custom-designed software containing data mining tools, a BioMAP® profile can be compared against a proprietary reference database of >4,000 BioMAP® profiles of bioactive agents (biologics, approved drugs, chemicals and experimental agents) to classify and identify the most similar profiles. This robust data platform allows rapid evaluation and interpretation of BioMAP® profiles by performing the unbiased mathematical identification of similar activities. Specific BioMAP® activities have been correlated to in vivo biology, and multiparameter BioMAP® profiles have been used to distinguish compounds based on MoA and target selectivity and can provide a predictive signature for in vivo toxicological outcomes (e.g., vascular toxicity, developmental toxicity, etc.) across diverse physiological systems.

Human primary cells in BioMAP® systems are used at early passage (passage 4 or earlier) to minimize adaptation to cell culture conditions and preserve physiological signaling responses. All cells are from a pool of multiple donors (n=2-6), commercially purchased and handled according to the recommendations of the manufacturers. Human blood derived CD14+ monocytes are differentiated into macrophages in vitro before being added to the Mphg system. Abbreviations are used as follows: Human umbilical vein endothelial cells (HUVEC), Peripheral blood mononuclear cells (PBMC), Human neonatal dermal fibroblasts (HDFn), B cell receptor (BCR), T cell receptor (TCR) and Toll-like receptor (TLR). Cell types and stimuli used in each system are as follows: 3C system [HUVEC+(IL-1β, TNFα and IFNγ)], 4H system [HUVEC+(IL-4 and histamine)], LPS system [PBMC and HUVEC+LPS (TLR4 ligand)], SAg system [PBMC and HUVEC+TCR ligands], BT system [CD19+B cells and PBMC+(α-IgM and TCR ligands)], BF4T system [bronchial epithelial cells and HDFn+(TNFα and IL-4)], BE3C system [bronchial epithelial cells+(IL-1β, TNFα and IFNγ)], CASM3C system [coronary artery smooth muscle cells+(IL-1β, TNFα and IFNγ)], HDF3CGF system [HDFn+(IL-1β, TNFα, IFNγ, EGF, bFGF and PDGF-BB)], KF3CT system [keratinocytes and HDFn+(IL-1β, TNFα, IFNγ and TGFβ)], MyoF system [differentiated lung myofibroblasts+(TNFα and TGFβ)] and lMphg system [HUVEC and M1 macrophages+Zymosan (TLR2 ligand)].

Systems are derived from either single cell types or co-culture systems. Adherent cell types are cultured in 96 or 384-well plates until confluence, followed by the addition of PBMC (Sag and LPS systems). The BT system consists of CD19+B cells co-cultured with PBMC and stimulated with a BCR activator and low levels of TCR stimulation. Test agents prepared in either DMSO (small molecules; final concentration ≤0.1%) or PBS (biologics) are added at the indicated concentrations 1-hr before stimulation, and remain in culture for 24-hrs or as otherwise indicated (48-hrs, MyoF system; 72-hrs, BT system (soluble readouts); 168-hrs, BT system (secreted IgG)). Each plate contains drug controls (e.g., legacy control test agent colchicine at 1.1 µM), negative controls (e.g., non-stimulated conditions) and vehicle controls (e.g., 0.1% DMSO) appropriate for each system. Direct ELISA is used to measure biomarker levels of cell-associated and cell membrane targets. Soluble factors from supernatants are quantified using either HTRF® detection, bead-based multiplex immunoassay or capture ELISA. Overt adverse effects of test agents on cell proliferation and viability (cytotoxicity) are detected by sulforhodamine B (SRB) staining, for adherent cells, and alamarBlue® reduction for cells in suspension. For proliferation assays, individual cell types are cultured at subconfluence and measured at time points optimized for each system (48-hrs: 3C and CASM3C systems; 72-hrs: BT and HDF3CGF systems; 96-hrs: SAg system). Cytotoxicity for adherent cells is measured by SRB (24-hrs: 3C, 4H, LPS, SAg, BF4T, BE3C, CASM3C, HDF3CGF, KF3CT, and lMphg systems; 48-hrs: MyoF system), and by alamarBlue staining for cells in suspension (24-hrs: SAg system; 42-hrs: BT system) at the time points indicated.

Data Analysis is performed by dividing the measurements of the test agent by the average of control samples (at least 6 vehicle controls from the same plate) to generate a ratio that is then $\log_{10}$ transformed. Significance prediction envelopes are calculated using historical vehicle control data at a 95% confidence interval.

Biomarker activities are annotated when 2 or more consecutive concentrations change in the same direction relative to vehicle controls, are outside of the significance envelope and have at least one concentration with an effect size >20% ($|\log_{10}$ ratio$|>0.1$). Biomarker key activities are described as modulated if these activities increase in some systems, but decrease in others. Cytotoxic conditions are noted when total protein levels decrease by more than 50% ($\log_{10}$ ratio of SRB or alamarBlue levels <−0.3) and are indicated by a thin black arrow above the X-axis. A compound is considered to have broad cytotoxicity when cytotoxicity is detected in 3 or more systems. Concentrations of test agents with detectable broad cytotoxicity are excluded from biomarker activity annotation and downstream benchmarking, similarity search and cluster analysis. Antiproliferative effects are defined by an SRB or alamarBlue® $\log_{10}$ ratio value <−0.1 from cells plated at a lower density and are indicated by grey arrows above the X-axis. Cytotoxicity and antiproliferative arrows only require one concentration to meet the indicated threshold for profile annotation.

Example 3.2: The BioMAP® Profile for 3,5-bis(3,4-dihydro-2H-pyrrol-2-yl)pyridine A BioMAP® profile was generated for 3,5-bis(3,4-dihydro-2H-pyrrol-2-yl)pyridine as described in Example 3.1 above.

3,5-bis(3,4-dihydro-2H-pyrrol-2-yl)pyridine was found to be not cytotoxic at the concentrations tested in this study.

3,5-bis(3,4-dihydro-2H-pyrrol-2-yl)pyridine was found to be antiproliferative to human primary endothelial cells (100 μM, 33 μM, 11 μM), T cells (100 μM, 33 μM), B cells (100 μM, 33 μM, 11 μM), and fibroblasts (100 μM).

3,5-bis(3,4-dihydro-2H-pyrrol-2-yl)pyridine was found to impact inflammation-related activities as demonstrated by decreased Eotaxin 3, MCP-1, VCAM-1, MIG, IL-6, and P-selectin; increased sPGE2; and modulated sTNFα, IL-8. 3,5-bis(3,4-dihydro-2H-pyrrol-2-yl)pyridine was found to impact immunomodulatory activities as demonstrated by decreased CD40, sIgG, sIL-1β, HLA-DR, sIL-17A, CD38, sIL-6, sIL-17F, and sIL-2. 3,5-bis(3,4-dihydro-2H-pyrrol-2-yl)pyridine was found to impact tissue remodeling activities as demonstrated by decreased TIMP-1, Collagen IV, MMP-1, PAI-1, uPAR, alphaSMA, and MMP9. 3,5-bis(3,4-dihydro-2H-pyrrol-2-yl)pyridine was found to impact hemostasis-related activities as demonstrated by decreased TM; and increased TF. In addition, 3,5-bis(3,4-dihydro-2H-pyrrol-2-yl)pyridine was found to decrease LDLR.

See Table 5 for further description of these markers and associated BioMAP® systems.

Example 4

Characterization of 3,5-bis(3,4-dihydro-2H-pyrrol-2-yl)pyridine in the BioMAP® Non-Small Cell Lung Cancer (NSCL) panel 2 of the human primary cell-based systems. The tested compound in Example 4 has the structure:

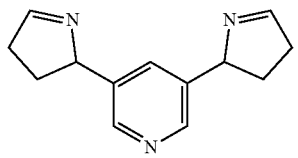 [SMILES: C1=NC(c2cncc(C3CCC=N3)c2)CC1]

The BioMAP® oncology system used in this Example is a coculture of primary human immune cells with primary tissue cells in the presence of the NSCL cells. In particular, The BioMAP® Oncology NSCLC panel models the interactions between the immune-stromal (fibroblasts) and immune-vascular (endothelial cells) environments in the context of non-small lung cancer (NCI-H1299 NSCLC cell line). The interactions between tumor cells, stimulated immune cells (peripheral blood mononuclear cells [PBMC]), and the host stromal network (human neonatal dermal fibroblasts [HDFn]) are captured in the StroNSCLC system. In parallel, the VascNSCLC system captures the interactions between tumor cells, activated immune cells and the vascular tissue (human umbilical vein endothelial cells [HUVEC]). The biomarkers selected for the BioMAP® Non-small Cell Lung Cancer (NSCLC) panel inform on activities related to inflammation, immune-function, tissue remodeling and metastasis in the context of a host tumor-microenvironment.

A signature BioMAP® profile that is reflective of the changes in protein biomarker readouts within an individual system is generated for each test agent. Biomarker readouts selected for therapeutic and biological relevance are predictive for disease outcomes or specific drug effects, and have been validated using agents with known clinical efficacy. Each readout is measured quantitatively by immune-based receptors, cytokines, chemokines, matrix molecules and enzymes. In total, the 42 biomarker readouts in the NSCLC panel capture the biological changes that occur within the physiological context of each particular BioMAP® system.

The BioMAP® Non-small Cell Lung Cancer (NSCLC) panel allows a focused in vitro evaluation of the impact of an agent in a model system that includes the hierarchical signaling networks that exist between interacting pathways and cells in a disease relevant setting. To represent the changes that are occurring in these complex systems, biomarker readouts with the ability to integrate and distinguish changes in different regulatory networks have been selected.

Table 6 below shows the results of testing 3,5-bis(3,4-dihydro-2H-pyrrol-2-yl)pyridine in the BioMAP® NSCLC system. 3,5-bis(3,4-dihydro-2H-pyrrol-2-yl)pyridine was used at concentrations of 7.4 μM, 22 μM, and 67 μM.

3,5-bis(3,4-dihydro-2H-pyrrol-2-yl)pyridine was found to be cytotoxic at 200 μM. Vehicle alone was used as negative control.

Data analysis of the results was performed as described in detail above in Example 3.1. Briefly, biomarker activities are annotated when at least one concentration of the test agent is outside of the significance envelope with an effect size >20% compared to the vehicle control (|log 10 ratio|>0.1) and a p-value <0.01. Cytotoxic conditions are noted when total protein levels decrease by more than 50% (log 10 ratio of SRB <−0.3). Biomarker key activities are described as modulated if these activities increase in some systems, but decrease in others. Concentrations that demonstrate cytotoxicity have been removed.

TABLE 6

| Biological and Disease relevance category | Decreased activity | Increased activity |
| --- | --- | --- |
| Inflammation related activities | STNFa, VCAM-1, SMDC | IP-10 |
| Matrix remodeling activities |  | EGFR, Col-III, HGF |
| Angiogenesis related activities | uPA | tPA |
| Immune-related activities | SIL-4, SIL-13, SIFNG, sGranB, sIL-10, sIL-2, SIL-17A, and sIL-6 |  |

Table 7 provides description of the biomarkers indicated in Table 6.

3,5-bis(3,4-dihydro-2H-pyrrol-2-yl)pyridine was found to impact inflammation-related activities (decreased sTNFα, VCAM-1, sMDC; increased IP-10), matrix remodeling activities (increased HGF, EGFR, Collagen III), angiogenesis-related activities (decreased uPA; increased tPA), and immune-related activities (decreased sIL-4, sIL-13, sIFNγ, sGranB, sIL-10, sIL-2, sIL-6, sIL-17A).

In conclusion, 3,5-bis(3,4-dihydro-2H-pyrrol-2-yl)pyridine had detectable cytotoxicity in the VascNSCLC system at 200 μM. 3,5-bis(3,4-dihydro-2H-pyrrol-2-yl)pyridine was active with 21 annotated readouts in BioMAP® Oncology NSCLC Panel. 23,5-bis(3,4-dihydro-2H-pyrrol-2-yl)pyridine showed a higher activity in the StroNSCLC system with 16 annotated activities and five in the VascNSCLC system. 3,5-bis(3,4-dihydro-2H-pyrrol-2-yl)pyridine impacted inflammation-related activities, matrix remodeling activities, angiogenesis-related activities, and immune-related activities.

TABLE 7

Abbreviations and descriptions of biomarkers

| Biomarker | Description |
| --- | --- |
| STNFa | Soluble Tumor Necrosis Factor a is a proinflammatory cytokine |
| VCAM-1 | Vascular Cell Adhesion Molecule-1 is a cell adhesion molecule mediating cell adhesion of monocytes and T cells to endothelial cells. |
| sMDC | Soluble Monocyte-derived chemokine mediates T regulatory cell recruitment |
| IP-10 | Interferon gamma induced protein 10 is antiangiogenetic and positively related to cancer patient survival |
| EGFR | Epidermal growth factor receptor (EGFR) is involved in cell proliferation and differentiation |
| Col-I | Collagen I is involved in tissue remodelling |
| Col-III | Collagen III is involved in cell adhesion |
| Col-IV | Collagen IV is involved in forming the basal lamina and its downregulation correlates with invasion of cancer cells |
| HGF | Hepatocyte growth factor is highly angiogenic |
| uPA | Urokinase plasminogen activator directs cellular migration |
| tPA | Tissue plasminogen activator regulates clot degradation and is involved in migration |
| SIL-4 | Soluble interleukin-4 inhibits Th1 cells and IFN gamma productions |
| SIL-13 | Soluble interleukin-13 is similar and is associated with cancer invasion |
| SIFNG | Soluble interferon gamma promotes immune response against viral infections, and exhibits context dependent anti or pro tumor activities |
| sGranB | Soluble Granzyme B mediates apoptosis of infected or malignant target cells |
| SIL-10 | Soluble interleukin-10 suppresses Th1 responses |
| SIL-2 | Soluble interleukin-2 promotes T cell proliferation and maturation, and favors an anti-tumor immune response |
| SIL-17A | Soluble interleukin-17A is a pro-inflammatory cytokine and is secreted by Th17 cells, and may be both pro-tumor by inducing angiogenesis and metastasis, and anti-tumor by inducing cytolytic T cell functions |
| SIL-6 | Soluble interleukin-6 is a proinflammatory cytokine that promotes proliferation and suppression of apoptosis in cancer cells |
| MCP-1 | Monocyte chemoattractant protein-1 is chemokine that attracts monocytes and T cells to sites of inflammation |
| MIG | Monokine induced by gamma interferon and MIG mediates T cell recruitment |
| TIMP2 | Tissue inhibitor of matrix metalloproteinase that is involved in tissue remodeling, angiogenesis, and fibrosis |
| MMP9 | Metalloproteinase 9 is involved in tissue remodeling and plays a role in tumor growth |
| PAI-I | Plasminogen activator inhibitor-1 is involved in tissue remodeling and tumor invasion, metastasis and angiogenesis |
| CEACAM5 | Carcinoembryonic antigen related cell adhesion molecule 5 is involved in cell adhesion and is a biomarker for gastrointestinal cancer |
| sVEGF | Soluble vascular endothelial growth factor is involved in angiogenesis. |
| Keratin 20 | Keratin 20 is a marker of colorectal adenocarcinoma |
| CD40 | CD40 is a cell surface adhesion receptor |
| CD69 | CD69 is an early marker of activated T cells |

Example 5

Characterization of 3,5-bis(3,4-dihydro-2h-pyrrol-2-yl)pyridine in the BioMAP® Colorectal Cancer of Human Primary Cell-Based Systems.

The BioMAP® oncology system used in this Example is a coculture of primary human immune cells with primary tissue cells in the presence of the Colorectal Cancer (CRC) cells. In particular, The BioMAP® Oncology CRC panel models the interactions between the immune-stromal (fibroblasts) and immune-vascular (endothelial cells) environments in the context of colorectal cancer (HT-29 colorectal adenocarcinoma cell line). The interactions between tumor cells, stimulated immune cells (peripheral blood mononuclear cells [PBMC]), and the host stromal network (human neonatal dermal fibroblasts [HDFn]) are captured in the StroHT29 system. In parallel, the VascHT29 system captures the interactions between tumor cells, activated immune cells and the vascular tissue (human umbilical vein endothelial cells [HUVEC]). The biomarkers selected for the BioMAP® Colorectal Cancer (CRC) panel inform on activities related to inflammation, immune-function, tissue remodeling and metastasis in the context of a host tumor-microenvironment.

A signature BioMAP® profile that is reflective of the changes in protein biomarker readouts within an individual system is generated for each test agent. Biomarker readouts selected for therapeutic and biological relevance are predictive for disease outcomes or specific drug effects, and have been validated using agents with known clinical efficacy. Each readout is measured quantitatively by immune-based receptors, cytokines, chemokines, matrix molecules and enzymes. In total, the 41 biomarker readouts in the CRC panel capture the biological changes that occur within the physiological context of each particular BioMAP® system.

The BioMAP® CRC panel allows a focused in vitro evaluation of the impact of an agent in a model system that includes the hierarchical signaling networks that exist between interacting pathways and cells in a disease relevant setting. To represent the changes that are occurring in these complex systems, biomarker readouts with the ability to integrate and distinguish changes in different regulatory networks have been selected.

Table 8 below shows the results of testing 3,5-bis(3,4-dihydro-2H-pyrrol-2-yl)pyridine in the BioMAP® CRC system. 3,5-bis(3,4-dihydro-2H-pyrrol-2-yl)pyridine was used at concentrations of 7.4 μM, 22 μM, and 67 μM. 3,5-bis(3,4-dihydro-2H-pyrrol-2-yl)pyridine was found to be cytotoxic at 200 μM. Vehicle alone was used as negative control.

Data analysis of the results was performed as described in detail above in Example 3.1. Briefly, biomarker activities are annotated when at least one concentration of the test agent is outside of the significance envelope with an effect size >20% compared to the vehicle control (|log 10 ratio|>0.1) and a p-value <0.01. Cytotoxic conditions are noted when total protein levels decrease by more than 50% (log 10 ratio of SRB <−0.3). Biomarker key activities are described as modulated if these activities increase in some systems, but decrease in others. Concentrations that demonstrate cytotoxicity have been removed.

TABLE 8

| Biological and Disease relevance category | Decreased activity | Increased activity |
|---|---|---|
| Inflammation related activities | VCAM-1, IP-10, MCP-1, MIG, | |
| Matrix remodeling activities | TIMP2, Col-I, Col-III, Col-IV, MMP9 | |
| Angiogenesis related activities | uPA, tPA, PAI-I | SVEGF |
| Tumor-related activities | CEACAM5, Keratin 20 | |
| Immune-related activities | CD40, CD69, SIFNG, sGranB, sIL-10, sIL-2, SIL-17A, and sIL-6 | |

The markers indicated in Table 8 are further described in Table 7 above.

3,5-bis(3,4-dihydro-2H-pyrrol-2-yl)pyridine was found to impact inflammation-related activities (decreased VCAM-1, IP-10, MCP-1, MIG), matrix remodeling activities (decreased TIMP-2, Collagen I, Collagen III, Collagen IV, MMP-9), angiogenesis-related activities (decreased PAI-1, tPA, uPA; increased sVEGF), tumor-related activities (decreased CEACAM5, Keratin 20), and immune-related activities (decreased sIFNγ, sGranB, sIL-1β, sIL-2, sIL-6, CD40, CD69, sIL-17A).

While the invention has been described with respect to specific examples, those skilled in the art will appreciate that there are numerous variations and permutations of the above described systems and techniques that fall within the spirit and scope of the invention as set forth in the appended claims.

What is claimed is:

1. A compound which has the structure:

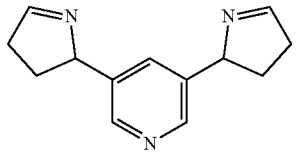 [SMILES: C1=NC(c2cncc(C3CCC=N3)c2)CC1]

or a pharmaceutically acceptable salt or solvate thereof.

2. A pharmaceutical composition comprising a therapeutically effective amount of a compound of claim 1 and a pharmaceutically acceptable vehicle therefor.

* * * * *